(12) United States Patent
St-Pierre

(10) Patent No.: US 8,396,670 B2
(45) Date of Patent: Mar. 12, 2013

(54) PROCESS, SYSTEM AND METHOD FOR IMPROVING THE DETERMINATION OF DIGESTIVE EFFECTS UPON AN INGESTABLE SUBSTANCE

(75) Inventor: Normand St-Pierre, Columbus, OH (US)

(73) Assignee: Venture Milling, Inc., Salisbury, MD (US)

( * ) Notice: Subject to any disclaimer, the term of this patent is extended or adjusted under 35 U.S.C. 154(b) by 1503 days.

(21) Appl. No.: 10/918,467

(22) Filed: Aug. 16, 2004

(65) Prior Publication Data

US 2006/0036370 A1 Feb. 16, 2006

(51) Int. Cl.
*G01N 33/50* (2006.01)

(52) U.S. Cl. .......................................... 702/19

(58) Field of Classification Search .................. None
See application file for complete search history.

(56) References Cited

U.S. PATENT DOCUMENTS

| | | | |
|---|---|---|---|
| 4,893,262 A | 1/1990 | Kalata | |
| 5,115,391 A | 5/1992 | Puthenpura et al. | |
| 5,313,212 A | 5/1994 | Ruzicka | |
| 5,534,271 A | 7/1996 | Ware et al. | |
| 5,645,834 A | 7/1997 | Cockrum | |
| 5,687,733 A | 11/1997 | McKown | |
| 5,714,185 A | 2/1998 | Mahadevan | |
| 5,767,080 A * | 6/1998 | Beck et al. ..................... | 514/12 |
| 5,955,122 A | 9/1999 | Petersen | |
| 6,017,563 A | 1/2000 | Knight et al. | |
| 6,357,429 B1 | 3/2002 | Carnevale et al. | |
| 6,384,384 B1 | 5/2002 | Connolly et al. | |
| 6,413,223 B1 | 7/2002 | Yang et al. | |
| 6,440,447 B1 | 8/2002 | Luhman | |
| 6,539,311 B1 | 3/2003 | Berger | |
| 6,542,858 B1 * | 4/2003 | Grass et al. ...................... | 703/2 |
| 6,575,905 B2 | 6/2003 | Knobbe et al. | |
| 6,645,834 B2 | 11/2003 | Akiyama | |
| 6,651,012 B1 | 11/2003 | Bechhoefer | |
| 7,479,392 B2 * | 1/2009 | Wandell et al. ............... | 436/71 |
| 2004/0018484 A1 * | 1/2004 | Wandell et al. ................... | 435/4 |

OTHER PUBLICATIONS

Tomankova et al.; Intestinal digestibility of crude protein in concentrates determined by a combined enzymatic method; Czech J. Anim. Sci. 2002, vol. 47, No. 1, pp. 15-20.
International Search Report for PCT International Application No. PCT/US05/28881, mailed Apr. 24, 2007.
Noftsger, et al., "Supplementation of Methionine and Selection of Highly Digestible Rumen Undergradable Protein to Improve Nitrogen Efficiency for Milk Production", J. Dairy Science, vol. 86, No. 3, pp. 958-969, 2003.
McCormick, et al., "Crude Protein and Rumen Undegradable Protein Effects on Reproduction and Lactation Performance of Holstein Cows", J. Dairy Science, vol. 82, No. 12, pp. 2697-2708, 1999.
Calsamiglia, et al., "A Three-Step in Vitro Procedure for Estimating Intestinal Digestion of Protein in Ruminants", J. Animal Science, vol. 73, pp. 1459-1465, 1995.
Zimmerman, et al., "Effect of Total and Rumen Undegradable Protein on the Performance of Cows Fed Low Fiber Diets", J. Dairy Science, vol. 75, pp. 1954-1964, 1992.
Stern, et al., "Alternative Techniques for Measuring Nutrient Digestion in Ruminants", J. Animal Science, vol. 75, pp. 2256-2276, 1997.
Maybeck, "Stochastic models, estimation, and control", vol. 1, 1999.
Bach, et al., "Evaluation of Selected Mathematical Approaches to the Kinetics of Protein Degradation in Situ", J. Animal Science, vol. 76, pp. 2885-2893, 1998.

* cited by examiner

*Primary Examiner* — Jason Sims
(74) *Attorney, Agent, or Firm* — Venable LLP; Steven J. Schwarz

(57) ABSTRACT

The present invention generally relates to processes, computer programs and systems, methods of making such and methods of using such for improving the determination of one or more digestive effects upon an ingestable substance. The underlying data used in this determination may originate from either an in vitro or in vivo analysis. The processes may be either partially or fully manual or automated, and combinations thereof.

22 Claims, 5 Drawing Sheets

PROCESS, SYSTEM AND METHOD FOR IMPROVING THE DETERMINATION OF DIGESTIVE EFFECTS UPON AN INGESTABLE SUBSTANCE

BACKGROUND OF THE INVENTION

1. Field of the Invention

The present invention generally relates to processes, computer programs and systems, methods of making them and methods of using them for improving the determination of one or more digestive effects upon an ingestable substance. The underlying data used in this determination may originate from either an in vitro or in vivo analysis. The processes may be either partially or fully manual or automated, and combinations thereof.

2. Related Art

U.S. Pat. No. 6,651,012 relates to techniques used in connection with determinating a health indicator (HI) of a component, such as that of an aircraft component. Techniques are described for estimating data values as an alternative to performing data acquisitions, as may be used when there is no pre-existing data.

U.S. Pat. No. 6,645,834 relates to a product and method of treating failure of passive immunity transfer and for stimulating growth and milk production in cows by administration of proteins purified from bovine colostrum is disclosed. Also administration in spray dried form as a diet supplement to growing calves or adult cows improves growth and milk production due to the presence of previously unappreciated nonspecific proteins.

U.S. Pat. No. 6,575,905 relates to a real-time glucose estimator using a linearized Kalman filter to determine a best estimate of glucose level in real time. The real-time glucose estimator can be implemented using a software algorithm.

U.S. Pat. No. 6,539,311 relates to an apparatus and method for measuring chemical, biological, nuclear agents in an environment includes several detectors capable of measuring concentrations of the agents in the environment and a processor capable of operating an algorithm which, based on two sequential measures of concentration of the agent, estimates decay or elevation rate of the concentrations of the agent and inputs this estimated change rate to a Kalman filter which predicts the next measurement.

U.S. Pat. No. 6,440,447 relates to the present invention concerns a method of enhancing milk production by a ruminant that includes providing a feed that contains sorbitol and at least one additional feed component, and orally feeding the feed to the ruminant.

U.S. Pat. No. 6,413,223 relates to a device for noninvasive, continuous monitoring of arterial blood pressure for advanced cardiovascular diagnoses. Simulation results indicate that the approach can generate an accurate estimation of the arterial blood pressure in real-time even from noisy sensor signals.

U.S. Pat. No. 6,384,384 relates to boil dry conditions are detected in utensils heated on a cooking appliance having at least one energy source disposed under a cooking surface such as a glass-ceramic plate and a controller for controlling the level of power supplied to the energy source. In one preferred embodiment, the portion of the controller that generates the derivative estimates is implemented as two Kalman filters.

U.S. Pat. No. 6,357,429 relates to the apparatus for estimating the richness of a mixture admitted into each of the combustion chambers of an engine having injectors comprising a sensor supplying an output signal that varies in substantially linear manner with richness and that is placed at the junction point between the exhausts from the chambers, and also comprises calculation means. The behavior model includes a submodel specific to each combustion chamber and having, for the chamber of order i, a Kalman filter having a coefficient matrix $C_{ij}$ and a specific gain matrix $K_{ij}$, where i corresponds to the number of the chamber and j corresponds to the number of the weighting coefficient.

U.S. Pat. No. 5,955,122 relates to methods of altering blood constituents in grazing animals. Improvement in body condition and body weight is concomitant with reduced milk production.

U.S. Pat. No. 5,767,080 relates to a method for enhancing milk production in dairy cows is disclosed herein. The method comprises feeding dairy cows a feed ration comprising silage made from corn plants that are homozygous for at least one bm gene and, coextensively in time, administering biologically active somatotropin to the cows.

U.S. Pat. No. 5,687,733 relates to cardiac output is separately estimated in a local estimator and a trend estimator to provide the cardiac output values. The local estimator preferably provides initial values to start a trend estimator.

U.S. Pat. No. 5,534,271 relates to a process for improving the utilization of feedstuffs by a ruminant, the process comprising the steps of mixing a lactic acid producing bacteria culture and a lactate utilizing bacteria culture, admixing these cultures with a dry formulation or an animal feedlot diet into a composition, and administering this composition orally to ruminants. The composition of the process is in a dry powder form for storage at ambient temperatures for long durations.

U.S. Pat. No. 5,313,212 relates to a radar system including a Kalman filter that processes radar return signals to produces position, velocity, acceleration, gain and residual error output signals, and a post-processor that processes these signals in accordance with a track filter bias estimation procedure.

U.S. Pat. No. 5,115,391 relates to making use of the conceptual and computational similarities between the Karmarkar method and the Kalman filter in a controller system that is capable of handling the observer function, the minimum time controller function and the minimum energy controller function. Different controls applied to the Kalman filter structure element and to the other elements of the system yielding control signals for control tasks.

U.S. Pat. No. 4,893,262 relates to a weight feeding system using a stochastic controller wherein the weight of material is sensed, and an estimate of the mass flow state of the material being discharged is created by use of a Kalman filter process. Feedback control tuning is also employed to monitor the set-point error in order to achieve quick response while maintaining smooth steady-state set point control.

S. Noftsger and N. R. St-Pierre, (2003), *J. Dairy Sci.* 86:958-969. Metabolizable protein (MP) supply and acid balance were manipulated through selection of highly digestible rumen-undegradable protein (RUP) sources and methionine (Met) supplementation. The supplementation of Met did not improve the efficiency of utilization during the digestibility study. Other results indicated that post-ruminal digestibility of RUP and amino acid balance can be more important than total RUP supplementation.

M. E. McCormick, D. D. French, T. F. Brown, G. J. Cuomo, A. M. Chapa, J. M. Fernandez, J. F. Beatty, and D. C. Blouin, (1999), *J. Dairy Sci.*, 82:2697-2708. A study to determine the effects of excess dietary crude protein (CP) and rumen undegradable protein (RUP) on reproduction and lactation performance of Holstein cows. Feeding grain diets that contained excess dietary protein impaired the reproductive performance of dairy cows grazing ryegrass.

Marshall D. Stern, Alex Bach, and Sergio Calsamiglia, (1997), *J. Anim. Sci.*, 75:2256-2276. Because in vivo measurement of nutrient digestion in the rumen and small intestine requires ruminally and intestinally cannulated animals that are expensive, labor-intensive, and subject to error associated with markers and inherent animal variation, alternative techniques have been developed. Researchers have proposed various in situ or in vitro procedures for estimating ruminal and small intestinal nutrient digestion. This review summarizes these alternative techniques.

Alex Bach. Marshall D. Stern. Neal R. Merchen, and James K. Drackley, (1998), *J. Anim. Sci.*, 76:2885-2893. A linear model, two mathematical nonlinear models, and a curve-peeling procedure were used to estimate rate and extent of ruminal CP degradation of meat and bone mean (MBM) and soybean mean (SBM) from data obtained using the in situ Dacron polyester bag technique.

Sergio Calsamiglia and Marshall D. Stern, (1995), *J. Anim. Sci.*, 73:1459-1465. A three-step in vitro procedure was developed to estimate intestinal digestion of proteins in ruminants. Because of variation, differences in intestinal digestion of proteins among and within various sources should be considered when determining protein value for ruminants.

C. A. Zimmerman, A. H. Rakes, T. E. Daniel and B. A. Hopkins, (1992), *J. Dairy Sci.*, 75:1954-1964. Soybean meal enhanced with rumen undegradable protein shows improved yields of milk and its components in primiparous cows fed low fiber diets, even when high protein diets were fed.

All documents cited herein are incorporated by reference for all purposes.

Background of the Technology
Analytical Chemistry in Studying Digestion

The study of digestion, while integral to all aspects of agriculture, has traditionally been difficult to address within the context of analytical chemistry. The digestive process is very complex in any organism, but particularly so in multicellular organisms wherein large variations in digestive effects occur at different stages in the process.

Collecting in vivo data is usually a very expensive undertaking for evaluating the degradability of an ingestable substance, particularly when the stage of the digestive process under analysis occurs entirely within the body of a subject. On the other hand, an in vitro model of a digestion can be very complex as it is necessary to incorporate a myriad of factors affecting any stage of the digestive process under analysis. Also, the data produced by either an in vitro or in vivo analysis will often be unreliable as the results can vary extensively in the degree of precision and accuracy that is achieved in the analysis due to the large number of factors that can affect the digestion of a substance after it has been ingested.

This difficulty in gathering accurate and precise data is compounded in any digestion process analysis using sequentially applied in vitro models for each stage of digestion. This is done to determine the overall digestive effects upon an ingested substance and will involve an in vitro model of each individual digestion stage. As data will ordinarily be gathered at each stage, this compounds the problem in assessing accuracy and precision from the data produced by the overall in vitro model.

Ruminant Digestion

The digestion of a ruminant (e.g., a cow) has been a subject of interest throughout history, but until recent times was guided almost exclusively by empirical observations. Only in recent years have there been any serious efforts to analyze the mechanics of the ruminant digestive process using analytical chemistry. This is due to the complexity and wide variations occurring in this particular type of digestive system.

The ruminant digestive process is focal to many aspects of modern agriculture. A major economic concern in dairy farming is the conversion of feedstuffs to milk. Likewise, the conversion of feed to meat guides decision-making in planning the ruminant diet in raising livestock for producing meat products. Also, the goal in producing both dairy and meat products is the efficient conversion of dietary feed, and the economic use of nutrients supplied by feedstuffs. Thus a more informed assessment of the effects a feed mixture will have upon a ruminant will impact decision-making for all the agricultural processes to which it is connected. Also ancillary to these goals is the environmental impact of the farming and feeding plans.

The increasing use of supplementary feeds has led to greater interest in cow nutrition and how best to meet these requirements. But, feeding strategies are often enigmatic to implement as the ruminant digestive process is unpredictable and difficult to calibrate for any given mix of feed. No simple answer or single recipe for feeding cows will suit all desired outcomes. Cow nutrition can be quite complex, the basic goal being to ascertain what the ruminants require and how best to meet these needs in a cost-effective and practical way. All sources of feed will eventually come under consideration: pasture, silage, hay, fodder crops, grains, pellets and by-products, as well as trace elements and mineral premixes. Forage, either preserved (hay, silage) or fed as pasture generally makes up the majority of the dairy cow diet, so the challenge is to evaluate and manage the feed process to be able to balance this diet using an array of feeding materials.

Three steps are involved in ruminants obtaining nutrients from their diet. First is ingestion, which is the physical act of taking food into the body. This is followed by digestion, in which the food is mechanically and chemically broken down to simpler chemical compounds. Finally, absorption occurs allowing some nutrients to pass from the digestive system into the blood stream.

The digestive system of the ruminant is well adapted to a diet of plant material. As ruminants, cows have one true stomach (the abomasum) and three other compartments (the rumen, the reticulum and the omasum), each having a specific role in the breakdown of the feed consumed. A representative ruminant digestive system is shown in FIG. 1. Once food has been ingested, it is briefly chewed and mixed with saliva, swallowed and passed down the esophagus into the rumen.

Ruminant Digestive Physiology

The rumen is the largest compartment of the adult ruminant stomach. It is adapted for the digestion of fiber and is sometimes described as a "fermentation vat." Its internal surface is covered with tiny projections called papillae; these increase the surface area of the rumen and allow better absorption of some digested nutrients, notably volatile fatty acids. The reticulum is separated from the rumen by a ridge of tissue. Its lining has a raised honeycomb-like pattern, also covered with small papillae. In an adult cow, the rumen and reticulum together have a capacity of about 50 to 120 liters of food and fluid.

The temperature inside the rumen remains stable at around 39° C. (38-42° C.) which is suitable for the growth of a range of micro-organisms. These microbes break down a feed mixture through a fermentation process. Under normal conditions, the pH of the contents of the rumen and reticulum is maintained in the range of 6-7, although it may be lower in grain-fed cows. The stable pH range is maintained by continual removal, via the rumen wall, of acidic end products of microbial fermentation, and by the addition of bicarbonate from the saliva. Saliva has several roles, including that it makes chewing and swallowing easier, but primarily, it has a chemical function deriving from it containing sodium (Na) and potassium (K) salts acting as buffering agents against acidity. A cow can produce 150 liters or more of saliva daily and the volume secreted depends upon the time to be spent eating and ruminating.

Before food reaches the rumen its breakdown has already begun by the mechanical action of chewing. Chemical breakdown is initiated by enzymes produced by the microbes in the rumen. The walls of the rumen and reticulum move continuously, churning and mixing the ingested feed with the rumen fluid (or 'digestive chemicals') and microbes. The contractions of the rumen and reticulum improve the flow of finer food particles into the next chamber, the omasum.

Rumination, or chewing the cud, is the process whereby newly eaten feed is returned to the mouth for further chewing. This extra chewing breaks the feed down into smaller pieces, thereby increasing its surface area. The smaller surface area in turn makes the feed more accessible to the chemicals which break it down. As a result, the rate of microbial digestion in the rumen is increased. The amount of time spent ruminating depends on the fiber content of the feed. The more fiber in the feed, the longer the ruminating time, therefore the less feed that can be eaten overall, and the less overall conversion to dairy or meat products. When any food is eaten by the cow, the predominant nutrients are initially in the form of carbohydrates, proteins and fats (or lipids). These are digested to products which can be used directly by the cow or by the microbes in the rumen.

Carbohydrate Digestion

Plant tissue dry matter is about 75% carbohydrate by weight. Microbial fermentation breaks the carbohydrates down into simple sugars. The microbes use these sugars as an energy source for their own growth and for making end products which are used by the cow. The end products of microbial fermentation of carbohydrates include: volatile fatty acids (mainly acetate, propionate and butyrate) and gases (carbon dioxide and methane). All carbohydrates can be fermented by rumen microbes, but the soluble and storage forms (starches) are fermented more quickly than the structural forms. Sugars and starches are broken down easily and quickly. By comparison, cell-wall material is digested slowly. As plants mature their cell walls become lignified. The lignin reduces the availability and utilization of structural carbohydrates. In other words, as plants mature their digestibility declines because the components of their cell walls become less accessible and harder to digest.

Soluble carbohydrates are digested 100 times faster by the microbes in the rumen than are storage carbohydrates, and storage carbohydrates are digested about five times faster than the structural carbohydrates. The bacteria which digest structural carbohydrates, such as cellulose and hemicellulose, produce a large proportion of acetic acid, which is important in the production of milkfat. These bacteria are sensitive to fats and acidity in the rumen. If a feed mixture contains too much fat or if the rumen becomes too acidic through feeding rapidly digestible carbohydrates, these bacteria can be completely eliminated or their growth rate inhibited. Reduction or elimination of these bacteria not only reduces the digestibility of the feed, it may also reduce the intake of feed. Once structural carbohydrates have passed through the rumen, there is little likelihood that they will be broken down further.

The bacteria that digest storage carbohydrates, or the starchy feeds such as cereal grains or potatoes are quite different from the cellulose-digesting bacteria. They are less sensitive to acidity and produce mainly propionic acid. Starches are rapidly fermented, and the lactic and propionic acid they produce causes acidity to increase in the rumen. The acidity caused by excess starch-digesting bacteria can suppress the bacteria which digest cellulose and thus reducing milkfat production. The bacteria that ferment feeds high in soluble sugars such as molasses, beets, turnips and good quality grass are similar to those that ferment starch. Sugary feeds generally cause fewer problems with increased acidity in the rumen than starchy feeds.

The most important end products of carbohydrate breakdown in the rumen are volatile fatty acids (VFAs). These acids are important because they are the major source of energy for the ruminant. The proportions in which they are produced determine fat and protein content of milk. The three major volatile fatty acids produced are acetate, propionate and butyrate. The ratio of the various VFAs produced depends on the type of feed being digested. Volatile fatty acids are absorbed through the walls of the rumen then transported in the bloodstream to the liver. In the liver they are converted to other sources of energy. From the liver, the energy produced is used to perform various functions such as milk production, maintenance of body systems, pregnancy and growth.

Lipid Digestion

Lipids (i.e., fats) are also a source of energy for the ruminant. Fats are either partially degraded and biohydrogenated in the rumen or assume a bypass or protected form. Fats are present in most of the more common dairy feeds in relatively small amounts. Protected fats, those which escape microbial digestion in the rumen, can be used to overcome the digestive upsets caused by high levels of rumen-degradable fat. The protected fats are readily digested and absorbed across the wall of the small intestine.

Protein Digestion

Protein, when digested, is broken down into peptides which are short chains of amino acids. Further digestion of peptides yields individual amino acids and eventually ammonia. The protein used by the ruminant may be from the feed mixture (dietary protein) or from the microbes washed from the rumen (microbial protein). The amount of each type depends on the extent to which dietary protein is degraded in the rumen and on the growth and outflow of microbes from the rumen.

Microbes in the rumen break down the rumen degradable protein (RDP) to amino acids then to ammonia. Ammonia is a major source of nitrogen for microbial growth. The microbes also convert non-protein nitrogen into ammonia. Microbes are continually 'flushed' from the reticulo-rumen, through the omasum to the next chamber, the abomasum, where they die and are digested by the cow. The amino acids produced when microbial protein is digested are then absorbed through the small intestine. The amount of microbial protein flowing to the intestines depends on the availability of energy and ammonia in the cows diet. If energy is limited, microbes become less efficient at using ammonia. Instead of being converted to microbial protein, the ammonia is absorbed across the rumen wall and into the bloodstream. In the liver, ammonia is then converted to urea. Most of this urea is excreted in the urine and some is recycled back into the rumen as non-protein nitrogen in saliva. When energy is in excess relative to protein, the rate of microbial protein synthesis declines. Total protein supply to the cow is reduced and milk yield and milk protein yield decreases. Excess energy is converted to body conditioning rather than to milk production.

Generally, pasture-based diets are relatively high in protein. The dietary protein that is directly available to the cow is rumen undegradable protein (RUP). A valuable proportion of this protein is then digested in the abomasum and small intestine. RUP provides a greater diversity of amino acids than does protein found in microbes.

Rumen degradable protein (RDP) is any protein in the diet that is broken down (digested) and of potential use by the microbes in the rumen. If enough energy (particularly carbohydrate) is available in the rumen, most of the digested RDP will be used to produce microbial protein. Undegradable dietary protein (RUP) is any protein in the diet that is not digested in the rumen. A variable proportion of RUP is dependent on the source and is digested in the lower gut.

The proportion of the protein in the diet which bypasses rumen digestion, and becomes RDP varies depending on how well the protein is protected from the microbes. This is shown diagrammatically in FIG. 2. A feed mixture can be treated with heat or chemicals to protect the protein. However, it is possible to over-protect protein and it then moves through the entire gut and out the other end without being digested. The RDP of feed also depends on how much is eaten in total, and how quickly the feed flows through the rumen. Greater intake and faster flow-through mean more protein becomes RDP because it simply escapes through the rumen before microbial breakdown occurs.

Factors Affecting Digestion

Some nutrients are absorbed across the rumen wall. Absorption involves the movement of individual feed components through the wall of the digestive tract into the blood stream by which they are transported to the liver. There is a constant flow of digestive material through the digestive tract. The passing of material through the rumen affects the extent of digestion. Generally, the rate of passage depends on density, particle size, ease of digestion and level of feeding. Some foods pass through the ruminant digestive system fairly quickly, but very indigestible food may be excreted over a long period.

The micro-organisms or microbes in the rumen include bacteria, protozoa and fungi. Bacteria and protozoa are the most significant microbes. Billions of bacteria and protozoa are found in the rumen where they digest dry matter in the feed mixture. Different species of bacteria and protozoa perform different functions. The numbers and proportions of each type of microbe depend on the individual animal's diet. Maintaining a proper mixture of different microbes is essential for keeping the rumen functioning efficiently. Dietary changes can cause a rapid change in the microbial population, which will also change the fermentation pattern and interfere with fiber digestion. Adjusting the level of grain fed must be done gradually so that the populations of rumen microbes can adjust accordingly. The speed of digestion of feeds depends on the quality and composition of the feed. It is also affected by the number and type of microbes, the pH in the rumen, the nutrients limiting the growth of the microbes, and the removal of microbes from the rumen. Energy and protein are the major nutrients which limit microbial growth and therefore rumen fermentation. The microbial population needs energy and protein for growth and multiplication. If either of these nutrients is in short supply, microbial growth is retarded, and so is the rate of digestion (the ruminal digestibility) of feed.

The omasum lies between the reticulum and abomasum. The material entering the omasum is made up of 90-95 percent cent water. The primary function of the omasum is to remove some of this water and to further grind and break down feed.

The abomasum connects the omasum to the small intestine. Acid digestion, rather than microbial fermentation, takes place in the abomasum, much the same as in the human stomach. The lining of the abomasum is folded into ridges which produce gastric juices containing hydrochloric acid and enzymes called pepsins. The pH of these gastric juices varies from 1 to 1.3 making the abomasum very acid, with a pH of about 2. The acidity in the abomasum kills the rumen microbes. The pepsins carry out the initial digestion of microbial and dietary protein in the abomasum.

From the abomasum the digested food moves to the small intestine. There, enzymes continue the digestion of feeds and microbes. Most nutrient absorption occurs in the small intestine. The large intestine, mainly the caecum and colon, is the site of secondary fermentation, particularly of fiber. Absorption of water, minerals and ammonia also occurs here. The components of feed not digested in the large intestine are passed through the rectum and anus and then expelled as waste.

Ruminant Diet Formulation

Formulating a diet is an important part of any feeding strategy. It is a means of meeting production and financial goals by feeding to the specific requirements of the ruminant in the most economical way. To formulate a diet, the skilled artisan needs to know the quantity of nutrients the cow or herd needs to meet production and animal health goals, and the nutrient content of the feeds. A balanced diet is one in which the animal nutrient requirements equals the nutrients available in the diet both from fermentation or direct digestion by the animal. Another consideration in balancing diet is whether the animal is physically able to eat the amount of feed intended to be provided. The final consideration is economics in that the economic response from feeding specific nutrients must exceed their cost.

Dietary requirements are calculated based upon production goals. Factors to consider are meat and milk production and composition, animal activity, weight, stage of pregnancy and changes in body condition. Diet formulation is largely a set of mathematical procedures combined with observation of the ruminant. The ruminant's ability to produce milk or enhanced body condition for meat depends largely on the feed eaten in terms of the intake of protein, energy and fiber. The feed must first be digested and the products of digestion absorbed into the blood from the digestive tract. How the animal uses or partitions the products of digestion are for maintenance, activity, pregnancy, milk production or body condition.

There are a range of products from the digestion of feeds consumed by the ruminant animal. These include ammonia, carbon dioxide, methane, volatile fatty acids, fats, undigested fiber, rumen microbes and undegradable protein. Some products of digestion are wasted, including carbon dioxide, methane, undigested fiber, and some are used by the animal. Fats from the diet or biosynthesized primarily from acetate by the liver, glucose from gluconeogenesis in the liver using predominantly propionate as the main precursor, and amino acids from post-ruminally digested microbial protein and RUP, circulate in the cow's blood stream ready for their role in metabolic processes. This is illustrated schematically in FIG. 3.

Milk is produced by udder tissue. About 500 liters of blood pass through the udder to produce one liter of milk. Blood delivers water, glucose, fats and amino acids to the udder. Cells in the udder tissue use these substances to form and secrete milk. Water in the milk comes from water in the blood. Lactose, milk sugar, is produced from the glucose, itself made from propionate in the liver. Milkfat comes from absorbed dietary fats, from de-novo synthesis using acetate as substrate and released body fat in the blood.

Milk protein, which is mostly casein, is built from the amino acids digested and absorbed from microbes and rumen undegradable protein in the blood using ATP (adenosine triphosphate) as an energy source to build the milk protein.

The level of fat and protein in milk varies, depending on the breed of cow, stage of lactation, and the diet. It follows, then, that the dollar value of milk varies too.

The udder makes milk protein from the amino acids and energy sources carried in the blood. Amino acids are the building blocks, and ATP provides the energy. ATP is derived from the catabolism of organic molecules by the alveolar cells. Sometimes amino acids are in catabolized to generate ATP as a source of energy. This is not an efficient use of feed because it wastes the protein-producing potential of the amino acids. Conversely, if ATP supply is plentiful but amino acids are in short supply or their relative supply is imbalanced, the building of milk protein will be limited. Any surplus of glucose may produce some lactose, but most will be stored; that is, the cow will put on body weight rather than produce milk. This also is not an efficient use of feed.

Milk protein and lactose production, and therefore milk volume, are related because milk protein and lactose serve as osmotic regulators in milk. The quantity of amino acids and the amount of glucose in the blood, ready for protein and lactose production, tend to be related to each other due to diet. A diet higher in energy often produces more rumen microbes, which are digested to amino acids; and a high-energy diet also produces more propionate, which converts to glucose. On the other hand, a diet higher in fiber often produces less microbes and more acetate, which converts to fats. Amino acids can be broken down to glucose if there is a shortage of glucose, but the reverse cannot occur.

Analytical Methods for Studying Digestion

The total amount of protein available for absorption is dependent upon the flow of microbial and dietary protein to the duodenum and also the intestinal digestibility of each type of protein source. It is possible to obtain estimates of the intestinal digestibility of any ingestable substance, including protein, using either in vivo or in vitro methodology. The in vivo methods, especially those for testing the digestive effect of regions below the first areas of the stomach are time-consuming, labor-intensive and require the use of surgically prepared animals. In vitro methods address some of these limitations by simulating various physiological conditions in the digestion of ruminants and other types of animals. One in vitro method, the Minnesota Three-Step Method was developed by Calsamiglia and Stern in 1995 (Calsamiglia et al., J. Anim. Science, v. 73: 1459-1465) and simulates two segments of the ruminant digestive process, Pepsin Digestion and Intestinal Digestion, using in vitro techniques, while a third area, the rumen itself, is tested using an in situ technique. This combination of techniques when calibrated properly is effective at roughly determining from the overall dietary protein in a given feed mixture the amount and percentage of rumen protein (RUP) in the dietary feed mixture and then the portion of the determined RUP that is then digested in the intestine (dRUP).

Precision and Accuracy

The individual test results of the directly measured RUP and dRUP of any feed mixture using these in vivo, in situ, and in vitro techniques tend to vary as the precision of the assay is poor. This calls into question the accuracy of any single result, and the potential that all results may be inaccurate depending upon how the methodology is calibrated. In all experimental measurements, there is a degree of uncertainty. This is usually dependent upon, among other things, the limitations of the measuring instrument or the skill of the person making the measurement. The instruments' built-in or inherent errors are called systematic errors. If a scale is not calibrated correctly, it will yield a reading that is consistently too high or too low. When errors are introduced by the skill or ability to read the scientific instruments, this will lead to results that may be either to high or too low. These are called random errors.

Although all experimental measurements are subject to error, the total number of repeated or related measurements can be evaluated in terms of their precision and accuracy. Precision indicates the reproducibility of a measurement. That is, the closeness in agreement among the values when the same quantity is measured several times. If the series of measurements is reproducible, then good precision is obtained as careful inspection of each measurement deviates only by a small amount from the average of the series. On the other hand, if there is a wide deviation among the series of measurements the precision is poor. A measurement is said to be accurate if it is close to the known "accepted" or "most probable" value. For example, the boiling point of pure water at sea level is 100° C. However a series measurements clustered very near 95° C. would be precise, since these figures show a high reproducibility yet inaccurate. However, the values are considerably off from the accepted value of 100° C. So, the measurements are not accurate.

On the other hand, a series of measurements averaging 100° C., but varying between 80° C. and 120° C. would be accurate yet imprecise. In this set of measurements, suspected inaccuracy may arise from a systemic error such as a miscalibrated thermometer.

Statistical Sampling

A sample is a subset of a population. Since it is usually impractical to test every member of a population, a sample from the population is typically the best approach available. Inferential statistics generally require that sampling be random although some types of sampling, such as those used in voter polling, seek to make the sample as representative of the population as possible by choosing the sample to resemble the population on the most important characteristics.

A biased sample is one in which the method used to create the sample results in samples that are systematically different from the population. It is important to realize that it is the method used to create the sample not the actual make up of the sample itself that defines the bias. A random sample that is very different from the population is not biased: it is by definition not systematically different from the population. It is randomly different.

Standard Deviation and Variance

The formula for the standard deviation is very simple: it is the square root of the variance. It is the most commonly used measure of the spread in data. The standard deviation has proven to be an extremely useful measure of spread in part because it is mathematically tractable. Many formulas in inferential statistics use the standard deviation.

The variance is a measure of how spread out a distribution is. It is computed as the average squared deviation of each number from its mean. The formula (in summation notation) for the variance in a population is:

$$\sigma^2 = \frac{\sum (X - \mu)^2}{N}$$

where $\mu$ is the population mean and N is the number of scores or measurements. When the variance is computed in a sample from a population, the statistic:

$$S^2 = \frac{\sum (X - M)^2}{N}$$

(where M is the mean of the sample) can be used.

However $S^2$ is a biased estimate of $\sigma^2$. A statistic is biased if it consistently over or underestimates the parameter it is estimating. In other words, it is biased if its expected value is not equal to the parameter. A stop watch that is a little bit fast gives biased estimates of elapsed time. Bias in this sense is different from the notion of a biased sample. A statistic is positively biased if it tends to overestimate the parameter; a statistic is negatively biased if it tends to underestimate the parameter. An unbiased statistic is not necessarily an accurate statistic. If a statistic is sometimes much too high and sometimes much too low, it can still be unbiased. But it would be very imprecise.

By far the most common formula for computing variance in a sample is:

$$s^2 = \frac{\sum (X-M)^2}{N-1}$$

which gives an unbiased estimate of $\sigma^2$. Since samples are usually used to estimate parameters, $s^2$ is the most commonly used measure of variance.

Regression Analysis

Regression is used to quantify the relationship between two or more continuous variables and to make predictions regarding the value of the dependent variables based on the levels of the independent variables. These predictions are made possible by knowing something about the values predicted. In other words, based on existing data values, predictions are made about other, similar values. Linear regression is used to make predictions about a single value. Simple linear regression involves discovering the equation for a line that most nearly fits the given data. That linear equation is then used to predict values for the data.

A regression equation is a mathematical equation that can be used to predict the values of one dependent variable from known values of one or more independent variables. Correlation describes the strength, or degree, of a linear relationship. That is, correlation allows the user to specify to what extent the two variables behave alike or vary together. Correlation analysis is used to assess the simultaneous variability of a collection of variables. The relationships among variables in a correlation analysis are generally not directional.

In order to make predictions, the user must examine the distribution of the data given. From this data, the user can then make a prediction about the problem being assessed. A predictor variable can be defined as a variable which is used to estimate some characteristic or response. A regression analysis which involves only one predictor is called simple linear regression analysis. Even though a single predictor may oversimplify the estimation in real systems, the results that are obtained can be easily extended to real systems.

The general regression equation can be written as y=a+b x. In order to predict a variable, the user needs to find the mean, variance, deviation and standard deviation of the values of x and y. The constants a and b in the regression equation are called the regression coefficients. The value of the constants a and b in the regression equation can be found out from the following two equations:

$a=Y-bX$ $b=(\Sigma xy-(\Sigma x)(\Sigma y)/n)/(\Sigma x^2-(\Sigma x)^2/n)$.

When the values of a and b are found, the regression equation can be written using these values. The regression line is the equation of the line of best fit for the data available. In other words, the error, which is the sum of the square of the vertical distance of each of the points from the regression line, is the smallest using this line.

Multiple regression is used to make predictions from multiple continuous variables. Use of multiple regression involves the discovering of the relationship between the values and then finding an equation that satisfies that relationship which considers if the variables are dependent or not. The equation has the form:

$k=ax+by+cz$.

This is called the regression equation of k on x, y and z. And the type of regression model is called a multiple regression model.

If there is a linear relationship between a dependent variable z and two independent variables x and y. Then there exists an equation connecting the variables which has the form $z=a+bx+cy$.

This is called a regression equation of z on x and y. If x is the dependent variable, a similar equation would be called a regression equation of x on y and z.

Bayesian Statistics

Bayesian approaches use prior probabilities in conjunction with observations to estimate posterior probabilities, resulting in higher accuracy than is possible with classical statistical techniques. Thus, the variability and uncertainty in data and decisions, inherent in a complex food chain, can be dealt with.

From the early part of this century until the 1970s there was basically only one theory of statistical inference, the frequentist approach. The modern Bayesian approach began as a serious alternative in the 1960s and 1970s. In the 1990s, new computational procedures have even made Bayesian methods the only viable approach for some important kinds of problems involving navigation and space travel.

The main distinguishing feature of the Bayesian approach is that it makes use of more information than the frequentist approach. Whereas the latter is based on analysis of what we could call 'hard data', that is data which are generally well-structured and derived from a well-defined observation process, Bayesian statistics also accommodates 'prior information' which is usually less well specified and may even be subjective. This makes Bayesian methods potentially more powerful, but also implies a need for extra care in their use.

Kalman Filtering

In 1960s, R. E. Kalman developed an approach using Bayesian methods to describe a recursive solution to the discrete-data linear filtering problem. Since that time, due in large part to advances in digital computing, the Kalman filter has been the subject of extensive research and application in the area of autonomous or assisted navigation.

The Kalman filter is a set of mathematical equations that provides an efficient computational recursive solution of the least-squares method. The filter is very powerful in several aspects: it supports estimations of past, present, and future states, and it can do so even when the precise nature of the modeled system is unknown. The Kalman filter has been used to solve problems in areas of engineering such as control systems to aircraft tracking via radar. It is a technique for accurately estimating the state of a dynamic system using a recursive algorithm. A general representation of how the Kalman filter is applied is shown in FIG. 4.

The main advantage of the Kalman filter algorithm over other adaptive algorithms is that it has a much faster rate of convergence to the optimal solution. It is also highly applicable to processing via a microprocessor thus it offers advantages to real-time applications such as those mentioned above. However, it has not been used in the unrelated field of agriculture or as a means of controlling or estimating agricultural production.

SUMMARY OF THE INVENTION

The present invention generally relates to processes, computer programs and systems, methods of making them and methods of using them for improving the determination of one or more digestive effects upon an ingestable substance. The underlying data used in this determination may originate from either an in vitro or in vivo analysis. The processes may be either partially or fully manual or automated, and combinations thereof.

The present invention generally relates to a method for improving ruminant digestion. More particularly, the present invention relates to a method for enhancing milk production, meat production, pasture conversion and for modulating the environmental impact of ruminant waste products.

An object of the invention is a mono-standard Kalman-filtering process for improving the determination of the undegraded percentage (U %) of an ingestable substance (IS) within a sample at an actual or simulated point along a digestive process in an organism, the process comprising the following steps:
  i) obtaining a value for a directly measured (DM) U % of the IS in a specimen of the sample;
  ii) obtaining a value for a DM U % of the IS in a specimen of a standard substance;
  iii) obtaining a corrected estimate of the accurate U % of the IS in the standard specimen by calculating a correction factor to the DM value of the standard specimen U % using Bayesian statistical analysis with respect to at least one prior determined DM U % value for both the sample and the standard; and
  iv) obtaining a corrected estimate of the accurate U % of the IS in the sample specimen by proportionally modifying the DM value of the sample U % by the same proportion applied in correcting the DM value of the standard U %.

Other objects of the invention are this process wherein at least one value originates from the data of an in-vivo assay, wherein at least one value originates from the data of an in-vitro assay, wherein at least one value originates from the data of a single-step in-vitro assay, wherein at least one value originates from the data of a multi-step in-vitro assay, wherein at least one value originates from the data of an in-vitro assay modeling a normal digestive process, wherein at least one value originates from the data of an in-vitro assay modeling a digestive process associated with an extra-normal health condition, wherein at least one step is performed using a computer program product, wherein at least one measurement is entered into a computer system, wherein at least one value is processed by a computer system, wherein the standard specimen comprises a substance that is less degradable when digestibility is compared with the sample specimen, wherein the standard specimen comprises blood meal and the substance is protein, wherein the standard specimen comprises a substance that is more degradable when digestibility is compared with the sample specimen, wherein the standard specimen comprises casein and the substance is protein, wherein the process further comprises modulating the protein content in the milk of a ruminant by feeding the ruminant a food mixture comprising a component that is the same as the sample, wherein the process further comprises modulating the protein production of a ruminant by feeding the ruminant a food mixture comprising a component that is the same as the sample, wherein the process further comprises modulating the body condition of a ruminant by feeding the ruminant a food mixture comprising a component that is the same as the sample, wherein the process further comprises modulating the overall feed intake or pasture usage by a ruminant by feeding the ruminant a food mixture comprising a component that is the same as the sample, wherein the process further comprises modulating the waste production by a ruminant by feeding the ruminant a food mixture comprising a component that is the same as the sample, and wherein the process further comprises taking a measure of the U % of the IS in the sample.

Another object of the invention is a mono-standard Kalman-filtering process for improving the determination of the undegradability percentage (U %) of an ingestable substance (IS) within a sample at an actual or simulated point along a digestive process in an organism, the process comprising the following steps:
  i) obtaining a value for U $\%_x$, which is the directly measured (DM) undegraded proportion of the IS in a specimen of the sample;
  ii) obtaining a value for U $\%_{stand}$, which is the DM undegraded proportion of the IS in a specimen of a standard;
  iii) obtaining c-U $\%_{stand}$, which is a corrected value for U $\%_{stand}$, by calculating c-U $\%_{stand}$ according to the equation:

$$c - U\ \%_{stand} = \frac{((M - U\ \%_{stand-p} * 1/\sigma^2 - U\ \%_{stand-p}) + (U\ \%_{stand} * 1/\sigma^2 - U\ \%_{stand}))}{(1/\sigma^2 - U\ \%_{stand-p} + 1/\sigma^2 - U\ \%_{stand})}$$

wherein M-U $\%_{stand-p}$ is the mean (M) of all prior direct measurements $(DM_s)$ of the IS in the standard, $\sigma^2$-U $\%_{stand-p}$ is the variance $(\sigma^2)$ of all prior direct measurements $(DM_s)$ of the IS in the standard, U $\%_{stand}$ is the DM undegraded proportion of the IS in a specimen of a standard determined in the same assay as the specimen of the sample, and $\sigma^2$-U $\%_{stand-p}$ is the inter-assay variance of U $\%_{stand}$.
  iv) obtaining c-U $\%_x$, which is a corrected value for U $\%_x$, by calculating c-U $\%_x$ according to the equation:

$$c\text{-}U\ \%_x = (c\text{-}U\ \%_{stand}/U\ \%_{stand}) * U\ \%_x.$$

Other objects of the invention are this process wherein at least one value originates from the data of an in-vivo assay, wherein at least one value originates from the data of an in-vitro assay, wherein at least one value originates from the data of a single-step in-vitro assay, wherein at least one value originates from the data of a multi-step in-vitro assay, wherein at least one value originates from the data of an in-vitro assay modeling a normal digestive process, wherein at least one value originates from the data of an in-vitro assay modeling a digestive process associated with an extra-normal health condition, wherein at least one step is performed using a computer program product, wherein at least one measurement is entered into a computer system, wherein at least one value is processed by a computer system, wherein the standard specimen comprises a substance that is less degradable when digestibility is compared with the sample specimen, wherein the standard specimen comprises blood meal and the substance is protein, wherein the standard specimen comprises a substance that is more degradable when digestibility is compared with the sample specimen, wherein the standard specimen comprises casein and the substance is protein, wherein the process further comprises modulating the protein content in the milk of a ruminant by feeding the ruminant a food mixture comprising a component that is the same as the sample, wherein the process further comprises modulating the protein production of a ruminant by feeding the ruminant a food mixture comprising a component that is the same as the sample, wherein the process further comprises modulating the body condition of a ruminant by feeding the ruminant a food mixture comprising a component that is the same as the sample, wherein the process further comprises modulating the overall feed intake or pasture usage by a ruminant by feeding the ruminant a food mixture comprising a component that is the same as the sample, wherein the process further comprises modulating the waste production by a ruminant by feeding the ruminant a food mixture comprising a component that is the same as the sample, and wherein the process further comprises taking a measure of the U % of the IS in the sample.

Another object of the invention is a di-standard Kalman-filtering process for improving the determination of the undegradeability percentage (U %) of an ingestable substance (IS) within a food mixture sample at an actual or simulated point along a digestive process in an organism, the process comprising the following steps:

i) obtaining a value for U $\%_x$, which is the directly measured (DM) undegraded proportion of the IS in a specimen of the sample;

ii) obtaining a value for U $\%_{stand-1}$, which is the DM undegraded proportion of the IS in a specimen of a first standard;

iii) obtaining a value for U $\%_{stand-2}$, which is the DM undegraded proportion of the IS in a specimen of a second standard;

iv) obtaining c-U $\%_{stand-1}$, which is a corrected value for U $\%_{stand-1}$, by calculating c-U $\%_{stand-1}$ according to the equation:

$$c-U\%_{stand-1} = \frac{((M - U\%_{stand-p1} * 1/\sigma^2 - U\%_{stand-p1}) + (U\%_{stand-1} * 1/\sigma^2 - U\%_{stand-1}))}{(1/\sigma^2 - U\%_{stand-p1} + 1/\sigma^2 - U\%_{stand-1})}$$

wherein M-U $\%_{stand-p1}$ is the mean (M) of all prior direct measurements (DM$_s$) of the IS in the first standard, $\sigma^2$-U $\%_{stand-p1}$ is the variance ($\sigma^2$) of all prior direct measurements (DM$_s$) of the IS in the first standard, U $\%_{stand-1}$ is the DM undegraded proportion of the IS in a specimen of the first standard determined in the same assay as the specimen of the sample, and $\sigma^2$-U $\%_{stand-1}$ is the inter-assay variance of U $\%_{stand-1}$.

v) obtaining c-U $\%_{stand-2}$, which is a corrected value for U $\%_{stand-2}$, by calculating c-U $\%_{stand-2}$ according to the equation:

$$c-U\%_{stand-2} = \frac{(M - U\%_{stand-p2} * 1/\sigma^2 - U\%_{stand-p2}) + (U\%_{stand-2} * 1/\sigma^2 - U\%_{stand-2})}{(1/\sigma^2 - U\%_{stand-p2} + 1/\sigma^2 - U\%_{stand-2})}$$

wherein M-U $\%_{stand-p2}$ is the mean (M) of all prior direct measurements (DM$_s$) of the IS in a second standard, $\sigma^2$-U $\%_{stand-p2}$ is the variance ($\sigma^2$) of all these prior direct measurements (DM$_s$) of the IS in the second standard, U $\%_{stand-2}$ is the DM undegraded proportion of the IS in a specimen of the second standard determined in the same assay as the specimen of the sample, and $\sigma^2$-U $\%_{stand-2}$ is the inter-assay variance of U $\%_{stand-2}$.

vi) obtaining a value for c-U $\%_x$, a corrected estimate for the accurate U % of the IS in the sample specimen by calculating the regression as follows:

setting $$X = \begin{bmatrix} 1 & U\%_{stand-1} \\ 1 & U\%_{stand-2} \end{bmatrix}, \quad Y = \begin{bmatrix} c - U\%_{stand-1} \\ c - U\%_{stand-2} \end{bmatrix}, \quad \text{and } B = \begin{bmatrix} B_0 \\ B_1 \end{bmatrix}$$

calculating

B=[X$^1$X]$^{-1}$ X$^1$Y, wherein X$^1$ is a transpose matrix of X and [ ]$^{-1}$ is the matrix inverse and obtaining values for B$_0$ and B$_1$, and obtaining a value for c-U $\%_x$, by calculating for c-U $\%_x$ according to the equation:

$$c-U\%_x = B_0 + (B_1 * U\%_x)$$

Other objects of the invention are this process wherein at least one value originates from the data of an in-vivo assay, wherein at least one value originates from the data of an in-vitro assay, wherein at least one value originates from the data of a single-step in-vitro assay, wherein at least one value originates from the data of a multi-step in-vitro assay, wherein at least one value originates from the data of an in-vitro assay modeling a normal digestive process, wherein at least one value originates from the data of an in-vitro assay modeling a digestive process associated with an extra-normal health condition, wherein at least one step is performed using a computer program product, wherein at least one measurement is entered into a computer system, wherein at least one value is processed by a computer system, wherein at least one standard specimen comprises a substance that is less degradable when digestibility is compared with the sample specimen, wherein at least one standard specimen comprises blood meal and the substance is protein, wherein at least one standard specimen comprises a substance that is more degradable when digestibility is compared with the sample specimen, wherein at least one standard specimen comprises casein and the substance is protein, wherein the process further comprises modulating the protein content in the milk of a ruminant by feeding the ruminant a food mixture comprising a component that is the same as the sample, wherein the process further comprises modulating the protein production of a ruminant by feeding the ruminant a food mixture comprising a component that is the same as the sample, wherein the process further comprises modulating the body condition of a ruminant by feeding the ruminant a food mixture comprising a component that is the same as the sample, wherein the process further comprises modulating the overall feed intake or pasture usage by a ruminant by feeding the ruminant a food mixture comprising a component that is the same as the sample, wherein the process further comprises modulating the waste production by a ruminant by feeding the ruminant a food mixture comprising a component that is the same as the sample, and wherein the process further comprises taking a measure of the U % of the IS in the sample.

Another object of the invention is a di-standard Kalman-filtering process for improving the determination of the undegraded percentage (U %) of an ingestable substance (IS) within a sample at an actual or simulated point along a digestive process in an organism, the process comprising the following steps:

i) obtaining a value for a directly measured (DM) U % of the IS in a specimen of the sample;

ii) obtaining a value for a DM U % of the IS in a specimen of a first standard;

iii) obtaining a value for a DM U % of the IS in a specimen of a second standard;
iv) obtaining a corrected estimate of the accurate U % of the IS in the first standard specimen by calculating a correction factor to the DM U % value of the first standard specimen using Bayesian statistical analysis with respect to at least one prior determined DM U % value for both the sample and the first standard;
v) obtaining a corrected estimate of the accurate U % of the IS in a second standard specimen by calculating a correction factor to the DM U % value for the second standard specimen using Bayesian statistical analysis with respect to at least one prior determined DM U % value for both the sample and the second standard;
v) obtaining a corrected estimate for the accurate U % of the IS in the sample specimen by modifying the DM value of the sample U % based on a regression analysis incorporating the correction made to the DM U % IS of each of the standards.

Other objects of the invention are this process wherein at least one value originates from the data of an in-vivo assay, wherein at least one value originates from the data of an in-vitro assay, wherein at least one value originates from the data of a single-step in-vitro assay, wherein at least one value originates from the data of a multi-step in-vitro assay, wherein at least one value originates from the data of an in-vitro assay modeling a normal digestive process, wherein at least one value originates from the data of an in-vitro assay modeling a digestive process associated with an extra-normal health condition, wherein at least one step is performed using a computer program product, wherein at least one measurement is entered into a computer system, wherein at least one value is processed by a computer system, wherein at least one standard specimen comprises a substance that is less degradable when digestibility is compared with the sample specimen, wherein at least one standard specimen comprises blood meal and the substance is protein, wherein at least one standard specimen comprises a substance that is more degradable when digestibility is compared with the sample specimen, wherein at least one standard specimen comprises casein and the substance is protein, wherein the process further comprises modulating the protein content in the milk of a ruminant by feeding the ruminant a food mixture comprising a component that is the same as the sample, wherein the process further comprises modulating the protein production of a ruminant by feeding the ruminant a food mixture comprising a component that is the same as the sample, wherein the process further comprises modulating the body condition of a ruminant by feeding the ruminant a food mixture comprising a component that is the same as the sample, wherein the process further comprises modulating the overall feed intake or pasture usage by a ruminant by feeding the ruminant a food mixture comprising a component that is the same as the sample, wherein the process further comprises modulating the waste production by a ruminant by feeding the ruminant a food mixture comprising a component that is the same as the sample, and wherein the process further comprises taking a measure of the U % of the IS in the sample.

Another object of the invention is a multi-standard Kalman-filtering process for improving the determination of the undegraded percentage (U %) of an ingestable substance (IS) within a food mixture sample at an actual or simulated point along a digestive process in an organism, the process comprising the following steps:
i) obtaining a value for a directly measured (DM) U % of the IS in a specimen of the sample;
ii) obtaining a value for a DM U % of the IS in a specimen of a first standard;
iii) obtaining a value for a DM U % of the IS in a specimen of at least one additional standard and repeating this step for any remaining standards;
iv) obtaining a corrected estimate of the accurate U % of the IS in the first standard specimen by calculating a correction factor to the DM U % value of the first standard specimen using Bayesian statistical analysis with respect to at least one prior determined DM U % value for both the sample and the first standard;
v) obtaining a corrected estimate of the accurate U % of the IS in at least one additional standard specimen by calculating a correction factor to the DM U % value for the first additional standard specimen using Bayesian statistical analysis with respect to at least one prior determined DM U % value for both the sample and the first additional standard and then repeating this step for any remaining standards;
vi) obtaining a corrected estimate for the accurate U % of the IS in the sample specimen by modifying the DM value of the sample U % based on a regression analysis incorporating the correction made to the DM U % IS of each of the standards.

Other objects of the invention are this process wherein at least one value originates from the data of an in-vivo assay, wherein at least one value originates from the data of an in-vitro assay, wherein at least one value originates from the data of a single-step in-vitro assay, wherein at least one value originates from the data of a multi-step in-vitro assay, wherein at least one value originates from the data of an in-vitro assay modeling a normal digestive process, wherein at least one value originates from the data of an in-vitro assay modeling a digestive process associated with an extra-normal health condition, wherein at least one step is performed using a computer program product, wherein at least one measurement is entered into a computer system, wherein at least one value is processed by a computer system, wherein at least one standard specimen comprises a substance that is less degradable when digestibility is compared with the sample specimen, wherein at least one standard specimen comprises blood meal and the substance is protein, wherein at least one standard specimen comprises a substance that is more degradable when digestibility is compared with the sample specimen, wherein at least one standard specimen comprises casein and the substance is protein, wherein the process further comprises modulating the protein content in the milk of a ruminant by feeding the ruminant a food mixture comprising a component that is the same as the sample, wherein the process further comprises modulating the protein production of a ruminant by feeding the ruminant a food mixture comprising a component that is the same as the sample, wherein the process further comprises modulating the body condition of a ruminant by feeding the ruminant a food mixture comprising a component that is the same as the sample, wherein the process further comprises modulating the overall feed intake or pasture usage by a ruminant by feeding the ruminant a food mixture comprising a component that is the same as the sample, wherein the process further comprises modulating the waste production by a ruminant by feeding the ruminant a food mixture comprising a component that is the same as the sample, and wherein the process further comprises taking a measure of the U % of the IS in the sample.

Another object of the invention is a mono-standard Kalman-filtering process computer program product for improving the determination of the undegraded percentage (U %) of an ingestable substance (IS) within a sample at an actual or simulated point along a digestive process in an organism, the computer program product comprising a computer usable medium having control logic stored therein for causing a computer to obtain a corrected value for the U % of the IS in a sample specimen, the control logic comprising:
  i) means for inputting or processing at least one value for a directly measured (DM) U % of the IS in a specimen of the sample;
  ii) means for inputting or processing at least one value for a DM U % of the IS in a specimen of a standard;
  iii) means for obtaining a corrected estimate of the accurate U % of the IS in the standard specimen by calculating a correction factor to the DM value of the standard specimen U % using Bayesian statistical analysis with respect to at least one prior determined DM U % value for both the sample and the standard; and
  iv) means for obtaining a corrected estimate of the accurate U % of the IS in the sample specimen by proportionally modifying the DM value of the sample U % by the same proportion applied in correcting the DM value of the standard U %.

Other objects of the invention are a method of making a computer program product comprising combining a first computer program product with a second computer program product to make a computer program product comprising the computer program product above, and a method of using the computer program product above, the method comprising inputting and/or processing data with the computer program product, or wherein at least one value originates from the data of an in-vivo assay, or wherein at least one value originates from the data of an in-vitro assay, or wherein at least one value originates from the data of a single-step in-vitro assay, or wherein at least one value originates from the data of a multi-step in-vitro assay, or wherein at least one value originates from the data of an in-vitro assay modeling a normal digestive process, or wherein at least one value originates from the data of an in-vitro assay modeling a digestive process associated with an extra-normal health condition, or wherein the method further comprises taking a measure of the U % of the IS in the sample.

Another object of the invention is a computer system for improving the determination of the undegraded percentage (U %) of an ingestable substance (IS) within a sample at an actual or simulated point along the digestive process of an animal, the computer system comprising at least one hardware component, and a computer usable medium having control logic stored therein wherein the control logic of the computer system contains all of the computer program product above, or wherein at least some portion of the computer program product is replaced by a hardware component in the computer system, and wherein the hardware component interacts with the remaining portion of the computer program product to perform the same function as the replaced portion of the computer program product.

Another object of the invention is a method of making a computer system comprising combining a computer program product and at least one hardware component to make a computer system comprising the computer system above.

Another object of the invention is a method of using the computer system above, the method comprising inputting and/or processing data with the computer program product. Other objects of the invention include this method of use, wherein at least one value originates from the data of an in-vivo assay, wherein at least one value originates from the data of an in-vitro assay, wherein at least one value originates from the data of a single-step in-vitro assay, wherein at least one value originates from the data of a multi-step in-vitro assay, wherein at least one value originates from the data of an in-vitro assay modeling a normal digestive process, wherein at least one value originates from the data of an in-vitro assay modeling a digestive process associated with an extra-normal health condition, or wherein the method further comprises taking a measure of the U % of the IS in the sample.

Another object of the invention is a mono-standard Kalman-filtering process computer program product for improving the determination of the undegraded percentage (U %) of an ingestable substance (IS) within a sample at an actual or simulated point along a digestive process in an organism, the computer program product comprising:
  a computer usable medium having control logic stored therein for causing a computer to obtain a corrected value for the U % of the IS in a sample specimen, the control logic comprising:
  i) a computer readable program code for causing the computer to input or process from a data field:
    a) a value for U $\%_x$, which is the directly measured (DM) undegraded proportion of the IS in a specimen of the sample;
    b) a value for U $\%_{stand}$, which is the DM undegraded proportion of the IS in a specimen of a standard;
    c) a value for M-U $\%_{stand-p}$ which is the mean (M) of all prior direct measurements ($DM_s$) of the IS in the standard;
    d) a value for $\sigma^2$-U $\%_{stand-p}$ which is the variance ($\sigma^2$) of all prior direct measurements ($DM_s$) of the IS in the standard;
    e) a value for U $\%_{stand}$ which is the DM of the undegraded proportion of the IS in a specimen of a standard determined in the same assay as the specimen of the sample;
    f) a value for $\sigma^2$-U $\%_{stand}$ which is the inter-assay variance of U $\%_{stand}$;
  ii) a computer readable program code for causing the computer to receive a definition of a rule associated with at least one data field, wherein the rule associates at least one threshold value with the data field to calculate c-U $\%_{stand}$, which is a corrected value for U $\%_{stand}$, by calculating c-U $\%_{stand}$ according to the equation:

$$c-U\%_{stand} = \frac{(M - U\%_{stand-p} * 1/\sigma^2 - U\%_{stand-p}) + (U\%_{stand} * 1/\sigma^2 - U\%_{stand})}{(1/\sigma^2 - U\%_{stand-p} + 1/\sigma^2 - U\%_{stand})} \text{ and}$$

iii) a computer readable program code for causing the computer to receive a definition of a rule associated with at least one data field, wherein the rule associates at least one threshold value with the data field to calculate c-U $\%_x$, which is a corrected value for U $\%_x$, by calculating c-U $\%_x$ according to the equation:

$$c-U\%_x = (c-U\%_{stand}/U\%_{stand}) * U\%_x.$$

Other objects of the invention are the computer program product above and further comprising an additional computer readable program code for causing the computer to display the calculated value for c-U $\%_x$, or further comprising an additional computer readable program code for causing the computer to input the calculated value for c-U $\%_x$ in a data field to receive a definition of a rule associated with the calculated value for c-U $\%_x$, wherein the rule associates at least one threshold value with the data field containing the calculated value for c-U $\%_x$, or further comprising an additional computer readable program code for causing the computer to input from a data field the prior population of U %$_{stand-p}$ DM values or instead further comprising an additional computer readable program code for causing the computer to receive a definition of a rule associated with the data field associated with the prior population of the U %$_{stand-p}$ DM values, wherein the rule associates at least one threshold value with the data field to calculate the mean and the variance of the prior population of the U %$_{stand-p}$ DM values, or further comprising an additional computer readable program code for causing the computer to input from a data field the prior population of U %$_{stand-p}$ DM values or instead further comprising an additional computer readable program code for causing the computer to receive a definition of a rule associated with the data field associated with the prior population of the U %$_{stand-p}$ DM values, wherein the rule associates at least one threshold value with the data field to calculate the mean and the variance of the prior population of the U %$_{stand-p}$ DM values.

Another object of the invention is a method of making a computer program product comprising combining a first computer program product with a second computer program product to make a computer program product comprising the computer program product of above, or a method of using the computer program product above, the method comprising inputting and/or processing data with the computer program product.

Other objects of the invention are the above method of use wherein at least one value originates from the data of an in-vivo assay, wherein at least one value originates from the data of an in-vitro assay, wherein at least one value originates from the data of a single-step in-vitro assay, wherein at least one value originates from the data of a multi-step in-vitro assay, wherein at least one value originates from the data of an in-vitro assay modeling a normal digestive process, wherein at least one value originates from the data of an in-vitro assay modeling a digestive process associated with an extra-normal health condition, or wherein the method further comprises taking a measure of the U % of the IS in the food mixture sample.

Another object of the invention is a computer system for improving the determination of the undegraded percentage (U %) of an ingestable substance (IS) within a food mixture sample at an actual or simulated point along the digestive process of an animal, the computer system comprising at least one hardware component, and a computer usable medium having control logic stored therein wherein the control logic of the computer system contains all of the computer program product above, or wherein at least some portion of the computer program product is replaced by a hardware component in the computer system, and wherein the hardware component interacts with the remaining portion of the computer program product to perform the same function as the replaced portion of the computer program product.

Other objects of the invention are a method of making a computer system comprising combining a computer program product and at least one hardware component to make a computer system comprising the computer system above, and a method of using the computer system above, the method comprising inputting and/or processing data with the computer program product or wherein the method further comprises taking a measure of the U % of the IS in the sample.

Another object of the invention is a di-standard Kalman-filtering process computer program product for improving the determination of the undegraded percentage (U %) of an ingestable substance (1S) within a sample at an actual or simulated point along a digestive process in an organism, the computer program product comprising:

a computer usable medium having control logic stored therein for causing a computer to obtain a corrected value for the U % of the IS in a sample specimen, the control logic comprising:

i) a computer readable program code for causing the computer to input or process from a data field:

a) a value for U %$_x$, which is the directly measured (DM) undegraded proportion of the IS in a specimen of the sample;

b) a value for U %$_{stand-1}$, which is the DM undegraded proportion of the IS in a specimen of a first standard;

c) a value for M-U %$_{stand-p1}$ which is the mean (M) of all prior direct measurements (DMs) of the IS in the first standard;

d) a value for $\sigma^2$-U %$_{stand-p1}$ which is the variance ($\sigma^2$) of all prior direct measurements (DMs) of the IS in the first standard;

e) a value for U %$_{stand-1}$ which is the DM of the undegraded proportion of the IS in a specimen of a first standard determined in the same assay as the specimen of the sample;

f) a value for $\sigma^2$-U %$_{stand-1}$ which is the inter-assay variance of U %$_{stand-1}$;

g) a value for U %$_{stand-2}$, which is the DM undegraded proportion of the IS in a specimen of a second standard;

h) a value for M-U %$_{stand-p2}$ which is the mean (M) of all prior direct measurements (DMs) of the IS in the second standard;

i) a value for $\sigma^2$-U %$_{stand-p2}$ which is the variance ($\sigma^2$) of all prior direct measurements (DMs) of the IS in the second standard;

j) a value for U %$_{stand-2}$ which is the DM of the undegraded proportion of the IS in a specimen of a second standard determined in the same assay as the specimen of the sample;

k) a value for $\sigma^2$-U %$_{stand-2}$ which is the inter-assay variance of U %$_{stand-2}$;

ii) a computer readable program code for causing the computer to receive a definition of a rule associated with at least one data field, wherein the rule associates at least one threshold value with the data field to calculate c-U %$_{stand-1}$, and c-U %$_{stand-2}$, which are corrected values for U %$_{stand-1}$ and U %$_{stand-2}$ respectively, by calculating c-U %$_{stand-1}$ and c-U %$_{stand-2}$ according to the equations:

$$c-U\%_{stand-1} = \frac{((M-U\%_{stand-p1} * 1/\sigma^2 - U\%_{stand-p1}) + (U\%_{stand-1} * 1/\sigma^2 - U\%_{stand-1}))}{(1/\sigma^2 - U\%_{stand-p1} + 1/\sigma^2 - U\%_{stand-1})}$$

$$c-U\%_{stand-2} = \frac{((M-U\%_{stand-p2} * 1/\sigma^2 - U\%_{stand-p2}) + (U\%_{stand-2} * 1/\sigma^2 - U\%_{stand-2}))}{(1/\sigma^2 - U\%_{stand-p2} + 1/\sigma^2 - U\%_{stand-2})} \text{ and}$$

iii) a computer readable program code for causing the computer to receive a definition of a rule associated with at least one data field, wherein the rule associates at least one threshold value with the data field to calculate a value for c-U %$_x$, a corrected estimate for the accurate U % of the IS in the sample specimen by calculating the regression as follows:

setting $$X = \begin{bmatrix} 1 & U\%_{stand-1} \\ 1 & U\%_{stand-2} \end{bmatrix}, \quad Y = \begin{bmatrix} c - U\%_{stand-1} \\ c - U\%_{stand-2} \end{bmatrix}, \text{ and } B = \begin{bmatrix} B_0 \\ B_1 \end{bmatrix}$$

calculating
B=$[X^1X]^{-1} X^1Y$, wherein $X^1$ is a transpose matrix of X and $[\,]^{-1}$ is the matrix inverse and obtaining values for $B_0$ and $B_1$, and
obtaining a value for c-U %$_x$, by calculating for c-U %$_x$ according to the equation:

$$c\text{-}U\%_x = B_0 + (B_1 * U\%_x).$$

Other objects of the invention are the computer program product above and further comprising an additional computer readable program code for causing the computer to display the calculated value for c-U %$_x$, or further comprising an additional computer readable program code for causing the computer to input the calculated value for c-U %$_x$ in a data field to receive a definition of a rule associated with the calculated value for c-U %$_x$, wherein the rule associates at least one threshold value with the data field containing the calculated value for c-U %$_x$, or further comprising an additional computer readable program code for causing the computer to input from a data field the prior population of U %$_{stand-p1}$ DM values and/or U %$_{stand-p1}$ DM values or instead further comprising an additional computer readable program code for causing the computer to receive a definition of a rule associated with the data field associated with the prior population of the U %$_{stand-p1}$ DM values and/or U %$_{stand-p2}$ DM values, wherein the rule associates at least one threshold value with the data field to calculate the mean and the variance of the prior population of the U %$_{stand-p1}$ DM values and/or U %$_{stand-p1}$ DM values, or further comprising an additional computer readable program code for causing the computer to input from a data field the prior population of U %$_{stand-p}$ DM values or instead further comprising an additional computer readable program code for causing the computer to receive a definition of a rule associated with the data field associated with the prior population of the U %$_{stand-p1}$ DM values and/or U %$_{stand-p2}$ DM values, wherein the rule associates at least one threshold value with the data field to calculate the mean and the variance of the prior population of the U %$_{stand-p1}$ DM values and/or U %$_{stand-p2}$ DM values.

Another objects is a method of making a computer program product comprising combining a first computer program product with a second computer program product to make a computer program product comprising the computer program product above, or a method of using the computer program product above, the method comprising inputting and/or processing data with the computer program product.

Other objects of the invention are the above method of use wherein at least one value originates from the data of an in-vivo assay, wherein at least one value originates from the data of an in-vitro assay, wherein at least one value originates from the data of a single-step in-vitro assay, wherein at least one value originates from the data of a multi-step in-vitro assay, wherein at least one value originates from the data of an in-vitro assay modeling a normal digestive process, wherein at least one value originates from the data of an in-vitro assay modeling a digestive process associated with an extra-normal health condition, or wherein the method further comprises taking a measure of the U % of the IS in the sample.

Another object of the invention is a computer system for improving the determination of the undegraded percentage (U %) of an ingestable substance (IS) within a food mixture sample at an actual or simulated point along the digestive process of an animal, the computer system comprising at least one hardware component, and a computer usable medium having control logic stored therein wherein the control logic of the computer system contains all of the computer program product above, or wherein at least some portion of the computer program product is replaced by a hardware component in the computer system, and wherein the hardware component interacts with the remaining portion of the computer program product to perform the same function as the replaced portion of the computer program product. Another object is a method of making a computer system comprising combining a computer program product and at least one hardware component to make a computer system comprising the computer system above.

Other objects of the invention are a method of using the computer system above, the method comprising inputting and/or processing data with the computer program product, or wherein the method further comprises taking a measure of the U % of the IS in the sample.

Another object of the invention is a di-standard Kalman-filtering process computer program product for improving the determination of the undegraded percentage (U %) of an ingestable substance (1S) within a sample at an actual or simulated point along a digestive process in an organism, the computer program product comprising
  a computer usable medium having control logic stored therein for causing a computer to obtain a corrected value for the U % of the IS in a sample specimen, the control logic comprising:
  i) means for inputting or processing at least one value for a directly measured (DM) U % of the IS in a specimen of the sample;
  ii) means for inputting or processing at least one value for a DM U % of the IS in a specimen of a first standard;
  iii) means for inputting or processing at least one value for a DM U % of the IS in a specimen of a second standard;
  iv) means for obtaining a corrected estimate of the accurate U % of the IS in the first standard specimen by calculating a correction factor to the DM U % value of the first standard specimen using Bayesian statistical analysis with respect to at least one prior determined DM U % value for both the sample and the first standard;
  v) means for obtaining a corrected estimate of the accurate U % of the IS in a second standard specimen by calculating a correction factor to the DM U % value for the second standard specimen using Bayesian statistical analysis with respect to at least one prior determined DM U % value for both the sample and the second standard;
  vi) means for obtaining a corrected estimate for the accurate U % of the IS in the sample specimen by modifying the DM value of the sample U % based on a regression analysis incorporating the correction made to the DM U % IS of each of the standards.

Another object of the invention is a method of making a computer program product comprising combining a first computer program product with a second computer program product to make a computer program product comprising the computer program product above, or a method of using the computer program product above, the method comprising inputting and/or processing data with the computer program product. Other objects are this method of use wherein at least one value originates from the data of an in-vivo assay, wherein at least one value originates from the data of an in-vitro assay, wherein at least one value originates from the data of a single-step in-vitro assay, wherein at least one value originates from the data of a multi-step in-vitro assay, wherein at least one value originates from the data of an in-vitro assay modeling a normal digestive process, wherein at least one value originates from the data of an in-vitro assay modeling a digestive process associated with an extra-normal health condition, or wherein the method further comprises taking a measure of the U % of the IS in the sample.

Another object of the invention is a computer system for improving the determination of the undegraded percentage (U %) of an ingestable substance (IS) within a sample at an actual or simulated point along the digestive process of an animal, the computer system comprising at least one hardware component, and a computer usable medium having control logic stored therein wherein the control logic of the computer system contains all of the computer program product above, or wherein at least some portion of the computer program product is replaced by a hardware component in the computer system, and wherein the hardware component interacts with the remaining portion of the computer program product to perform the same function as the replaced portion of the computer program product. Another object of the invention is a method of making a computer system comprising combining a computer program product and at least one hardware component to make a computer system comprising the computer system above.

Another object of the invention is a method of using the computer system above, the method comprising inputting and/or processing data with the computer program product. Other objects are this method of use wherein at least one value originates from the data of an in-vivo assay, wherein at least one value originates from the data of an in-vitro assay, wherein at least one value originates from the data of a single-step in-vitro assay, wherein at least one value originates from the data of a multi-step in-vitro assay, wherein at least one value originates from the data of an in-vitro assay modeling a normal digestive process, wherein at least one value originates from the data of an in-vitro assay modeling a digestive process associated with an extra-normal health condition, or wherein the method further comprises taking a measure of the U % of the IS in the sample.

Another object of the invention is a multi-standard Kalman-filtering process computer program product for improving the determination of the undegraded percentage (U %) of an ingestable substance (IS) within a sample at an actual or simulated point along a digestive process in an organism, the computer program product comprising:

a computer usable medium having control logic stored therein for causing a computer to obtain a corrected value for the U % of the IS in a sample specimen, the control logic comprising:

i) means for inputting or processing at least one value for a directly measured (DM) U % of the IS in a specimen of the sample;

ii) means for inputting or processing at least one value for a DM U % of the IS in a specimen of a first standard;

iii) means for inputting or processing at least one value for a DM U % of the IS in a specimen of at least one additional standard and repeating this step for any remaining standards;

iv) means for obtaining a corrected estimate of the accurate U % of the IS in the first standard specimen by calculating a correction factor to the DM U % value of the first standard specimen using Bayesian statistical analysis with respect to at least one prior determined DM U % value for both the sample and the first standard;

v) means for obtaining a corrected estimate of the accurate U % of the IS in a second standard specimen by calculating a correction factor to the DM U % value for the second standard specimen using Bayesian statistical analysis with respect to at least one prior determined DM U % value for both the sample and the first additional standard and then repeating this step for any remaining standards;

vi) means for obtaining a corrected estimate for the accurate U % of the IS in the sample specimen by modifying the DM value of the sample U % based on a regression analysis incorporating the correction made to the DM U % IS of each of the standards.

Another object of the invention is a method of making a computer program product comprising combining a first computer program product with a second computer program product to make a computer program product comprising the computer program product above, or a method of using the computer program product above, the method comprising inputting and/or processing data with the computer program product. Other objects are this method of use wherein at least one value originates from the data of an in-vivo assay, wherein at least one value originates from the data of an in-vitro assay, wherein at least one value originates from the data of a single-step in-vitro assay, wherein at least one value originates from the data of a multi-step in-vitro assay, wherein at least one value originates from the data of an in-vitro assay modeling a normal digestive process, wherein at least one value originates from the data of an in-vitro assay modeling a digestive process associated with an extra-normal health condition, or wherein the method further comprises taking a measure of the U % of the IS in the sample.

Another object of the invention is a computer system for improving the determination of the undegraded percentage (U %) of an ingestable substance (IS) within a sample at an actual or simulated point along the digestive process of an animal, the computer system comprising at least one hardware component, and a computer usable medium having control logic stored therein wherein the control logic of the computer system contains all of the computer program product above, or wherein at least some portion of the computer program product is replaced by a hardware component in the computer system, and wherein the hardware component interacts with the remaining portion of the computer program product to perform the same function as the replaced portion of the computer program product. Another object of the invention is a method of making a computer system comprising combining a computer program product and at least one hardware component to make a computer system comprising the computer system above.

Another object of the invention is a method of using the computer system above, the method comprising inputting and/or processing data with the computer program product. Other objects are this method of use wherein at least one value originates from the data of an in-vivo assay, wherein at least one value originates from the data of an in-vitro assay, wherein at least one value originates from the data of a single-step in-vitro assay, wherein at least one value originates from the data of a multi-step in-vitro assay, wherein at least one value originates from the data of an in-vitro assay modeling a normal digestive process, wherein at least one value originates from the data of an in-vitro assay modeling a digestive process associated with an extra-normal health condition, or wherein the method further comprises taking a measure of the U % of the IS in the sample.

BRIEF DESCRIPTION OF THE INVENTION

The present invention generally relates to processes, computer programs and systems, methods of making them and methods of using them for improving the determination of one or more digestive effects upon an ingestable substance. The invention incorporates the finding that a Kalman-filtering process can be combined with use of a standardized material aligned against the sample material being analyzed in a regression analysis to improve determination of the undegraded percentage (U %) of any ingestable substance (IS) within a sample at an actual or simulated point along the digestive process in an organism. The underlying data used in these determinations may originate from either an in vitro or in vivo analysis. The processes may be either partially or fully manual or automated, and combinations thereof.

In one embodiment, the analysis can be that of an ingestable substance in ruminant digestion. The invention also relates to the associated implications for these improved determinations within the field of agriculture, including systems and methods for enhancing milk production, meat production, pasture conversion and for modulating the environmental impact of ruminant waste. In one more specific consideration, the invention relates to improving the precision for the control of protein nutrition for ruminants including implementing a methodology for measuring protein degradability and digestibility in the rumen, and protein absorption both during and following processing in the rumen chamber of the ruminant.

DESCRIPTION OF THE FIGURES

The foregoing summary, as well as the following detailed description, will be better understood when read in conjunction with the appended drawings. For the purpose of illustrating the invention, there are shown in the drawings embodiments which are presently preferred, it being understood, however, that this invention is not limited to the precise arrangements and instrumentalities shown.

DETAILED DESCRIPTION OF THE INVENTION

Figure 1:
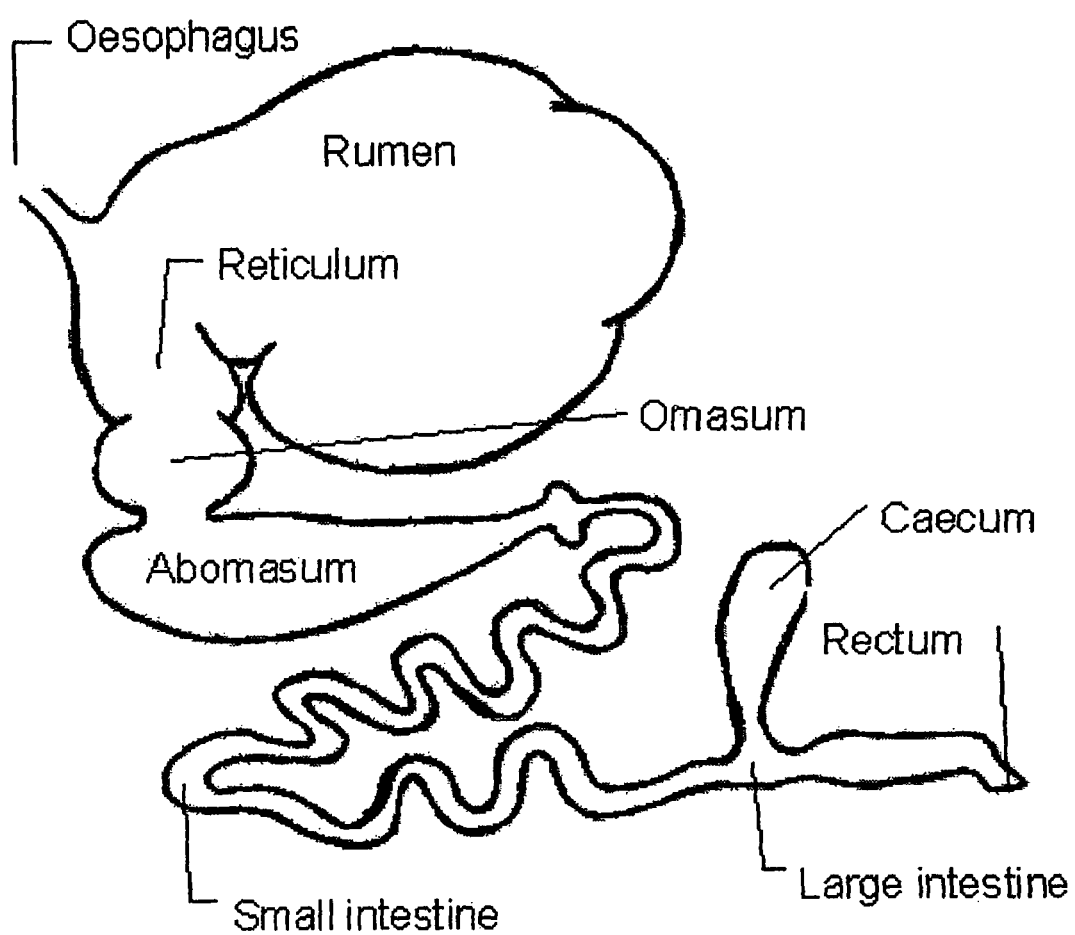
FIG. 1 is a frontal and abstracted view of a representative ruminant digestive system.
Figure 2:
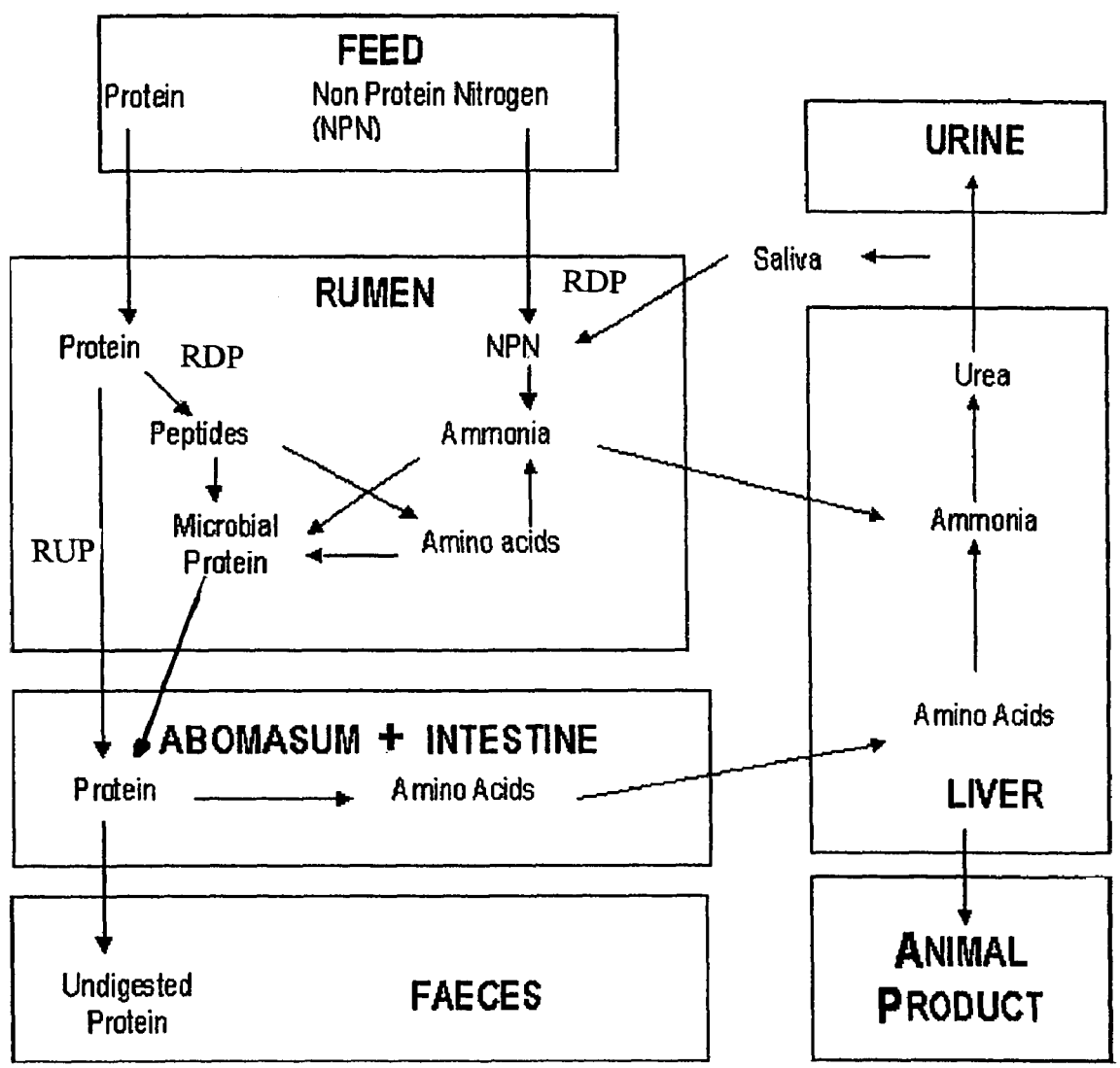
FIG. 2 is a schematic representation of the digestion, absorption and metabolism pathways for protein within a ruminant animal.
Figure 3:
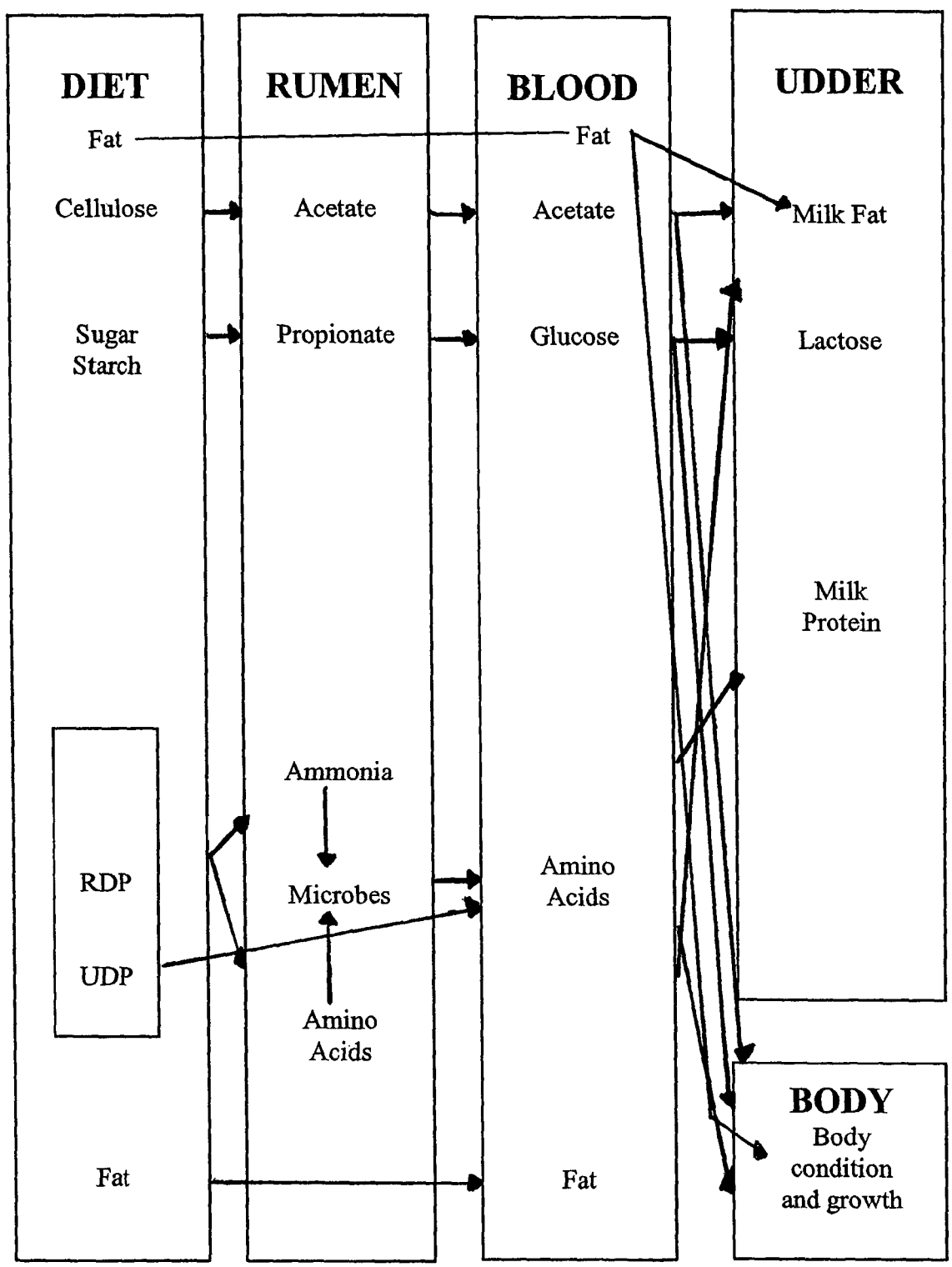
FIG. 3 is a schematic representation of the digestion, absorption and metabolism pathways for a complete dietary mixture within a ruminant animal.
Figure 4:
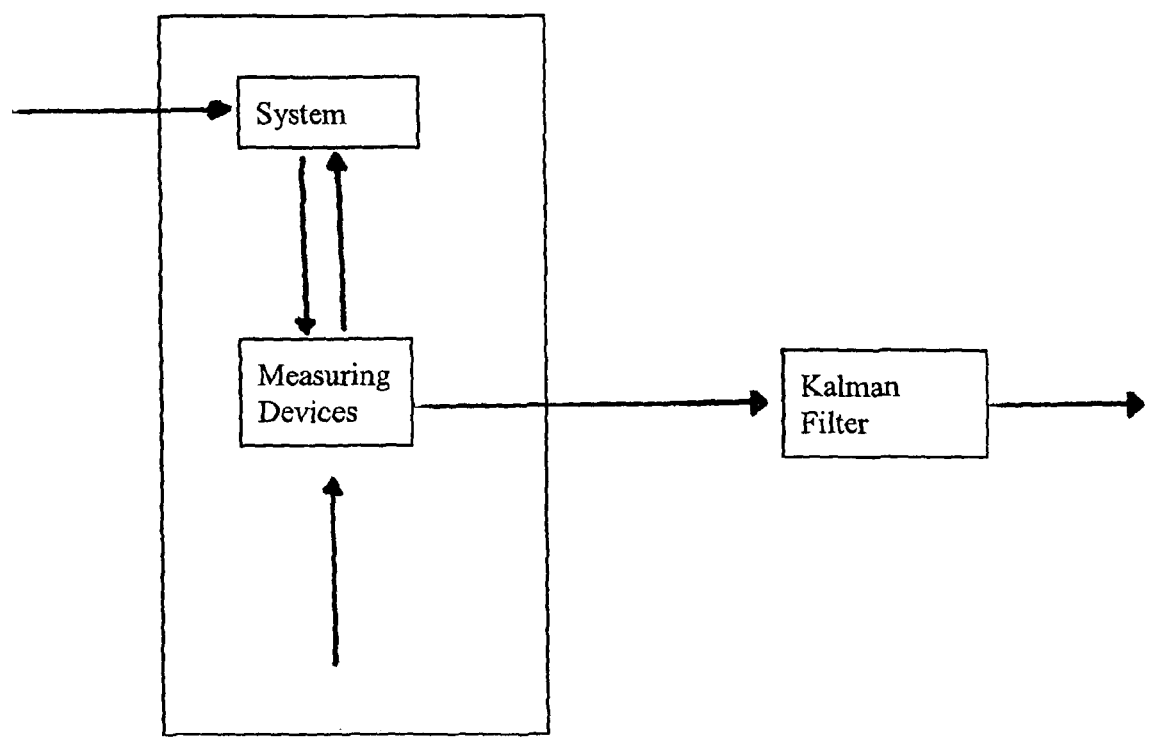
FIG. 4 is a generic schematic of how Kalman filtering is applied in processing the output of a measuring device that is monitoring a representative system.

While this invention is satisfied by embodiments in many different forms, there will herein be described in detail preferred embodiments of the invention, with the understanding that the present disclosure is to be considered as exemplary of the principles of the invention and is not intended to limit the invention to the embodiments illustrated and described. Numerous variations may be made by persons skilled in the art without departure from the spirit of the invention.

DEFINITIONS

An "organism" is any single-cell or multi-cellular animal or plant.

An "ingestable substance" is any identifiable substance that can be taken into a living organism and broken down into constituent parts by that organism, or other organisms within the host organism. The substance may be consumed for such purposes as driving the metabolism, body function or growth of the host organism, or for other purposes. The substance may be ingested in pure form or as part of a consumed food mixture, such as one or more type of protein, fat, carbohydrate or some inert material having an identifiable chemical or macromolecular structure when ingested and before being broken down within the organism into molecular constituents or chemical elements.

A "digestive process" is any single chemical, biological or physical action, and any grouping or combination of such actions within an organism associated with digestion or metabolism within the organism.

A "ruminant" is any animal that ruminates or uses a rumen or rumen-like stomach chamber as part of it's digestive process. A common ruminant is the cow. Other livestock can also be ruminant animals, including both sheep and goats. A ruminant can also be a wild-life species such as buffalo, elk, or deer.

Preferred Embodiments

Referring again to the method of Calsamiglia et al. developed at the University of Minnesota, and described herein as the "MN-3-Step" method, has been proposed to estimate the extent of protein degradation in the rumen of cattle. More specifically the MN-3-Step method has been proposed to estimate the fraction of the protein in a given feedstuff that is rumen undegradable (i.e., RUP) and the proportion of RUP that is digestible in the bovine lower digestive system (i.e., dRUP), digested within the intestine of the cow.

In applying the MN-3-Step method, it has become apparent that the overall assay is reliably accurate when applied across a substantially sized sample of assay results, but it is also very imprecise as the individual results lack reproducibility. As an example, Table 1 presents estimates of RUP and dRUP for a single sample of flash dried blood meal analyzed nine times over a period of nine weeks. The standard error, or imprecision, on a single measurement is approximately 8.8% units for RUP and 18.2% units for dRUP. Investigations show that the source of this variation in results is inter-assay (i.e, from between or among the assays) and not intra-assay (i.e., within the assay itself).

The following procedures were followed in implementing a modified Minnesota Three-Step in vitro procedure for estimating the Rumen-Undegradable Protein (RUP) and Intestinal Digestion of the RUP (dRUP). The procedures followed were a modification of the method shown by Calsamiglia and Stern.

Reagents:

HCl/pepsin solution: pH 1.9, I/V HC: solution with 1 g/L of pepsin (Sigma P-7012); 1 M NaOH solution; pancreatin solution (0.5 M $KH_2PO_4$ buffer [68.045 g/L of distilled water] standardized at pH 7.8 containing 50 ppm of thymil and 3 g/L of pancreatin (Sigma P-7545); and 100% (wt/vol) solution of trichloroaetic acid solution (TCA)

Procedures:

Feed samples were passed through a 2 mm screen. Weight was 1.5 grams of feed placed into 6 cm×10 cm Dacron polyester bag (enough replicates for 60 mg of residual N per feed, possibly 4-6 bags). The bags were suspended in the cow rumen for 16 hours. Bags were then rinsed with tap water until the runoff was clear. Samples were dried in a 55° C. oven for 48 hours. Samples of each feed were pooled and then nitrogen content determined by the method of Kjeldahl. Samples containing approximately 15 mg of residual nitrogen were then placed into a 50 ml centrifugation tube. A 10 ml HCl/pepsin solution was added, vortexed, and incubated for 1 hour in a 38° C. shaker bath.

After incubation, 0.5 mL of 1 N NaOH solution and 13.5 mL of pancreatin solution were added. Samples were vortexed and incubated at 38° C. for 24 hours in a shaker bath. Samples were vortexed approximately every 8 hours. After incubation, 3 mL of TCA solution were added to stop the enzymatic action and precipitate the undigested proteins. All tubes were then matrixed and allowed to stand for 15 minutes. These were centrifuged at 10,000×g for 15 minutes. The supernatant was analyzed for soluble nitrogen by the Kjeldahl method.

Procedure 2b. Analyze a sub-sample of intact feed material for amino acids according to Association of Official Analytical Chemists (AOAC) 932.30 E (a, b, c) Chapter 45.3.05, 1995. 2c. Include a sample of low digestibility blood (negative standard). 6b. Analyzed a sub-sample of the 16-hour residue for amino acids according to Association of Official Analytic Chemists (AOAC) 932.30 F (a, b, c) Chapter 45.3.05, 1995. 7b. Added a sample of laboratory grade casein (positive control). 15. Removed pellet (precipitate) from tube and analyze for amino acids according to Association of Official Analytical Chemists (AOAC) 932.30 E (a, b, c) Chapter 45.3.05, 1995.

Calculations:

For the calculation of RUP in the first step, rumen undegraded protein is calculated as in Calsamiglia and Stern. The correction is applied by applying a mono-standard Kalman filtering process using one standard. The same correction factor is applied to all amino acids.

For the calculation of dRUP, pepsin-pancreatin digestibility is calculated as in Calsamiglia and Stern, except that it is corrected by a di-standard Kalman-filtering process using two standards. The same correction method is applied to all amino acids.

TABLE 1

Estimates of RUP and dRUP for a single sample of blood meal done on nine consecutive weeks by the method of Calsamiglia et al. (MN-3-steps).

| Week | RUP (% of protein) | dRUP (% RUP) |
|---|---|---|
| 1 | 52.9 | 71.4 |
| 2 | 52.9 | 68.2 |
| 3 | 56.1 | 77.7 |
| 4 | 59.2 | 60.5 |
| 5 | 43.3 | 109.8 |
| 6 | 56.1 | 68.3 |
| 7 | 40.1 | 95.2 |
| 8 | 37.3 | 97.4 |
| 9 | 37.1 | 104.9 |
| Mean | 48.3 | 83.7 |
| Standard Deviation | 8.8 | 18.2 |

One aspect of the invention is that the use of one or more standard analytes yields a more precise result. The correction method, when applied to the sample results significantly improves their precision, thus reducing the number of replicates for the sample.

The standards chosen were batch-dried blood meal, because of its relatively low digestibility, and food grade casein, because of its very high digestibility. Measurements on these standards were used to correct measurements on other feedstuffs within the same batch of assays. Measurements on the standards, however, are not without errors. Statistical theory is therefore used to get optimal estimators from prior knowledge (i.e., prior measurements) and actual measurements on the standards in a given batch.

A process of merging a prior statistical distribution with measurements to yield a posterior statistical distribution is known as Bayesian statistics in a mathematical context, and Kalman filtering in an engineering context.

Example 1

Feedstuff A is assayed using the MN-3-step. At the same time, a sample of a blood meal standard and a sample of casein standard are also assayed. Measured RUP and dRUP are 85 and 90%, and 55 and 80% for sample A and standard blood meal, respectively, and that measured dRUP is 100% on the casein standard. Prior means are 40, 70 and 98% and prior variances are 77.7, 331.7, and 38.2 for the RUP of the blood meal, the dRUP of blood meal, and the dRUP of casein, respectively. Measurements were made in duplicates so the variances of the actual measurements are one half those of the priors. The calculations used for the mono-standard Kalman filter correction for the RUP and the di-standard Kalman filter correction for the dRUP are as follows.

1. Calculating a Corrected RUP for the Standard Blood Meal.

This is done by taking a weighed average of the prior RUP for the standard (40%) with the value of the actual measurement (55%), each weighed by the reciprocal of their variances (1/77.7 for the prior and 1/38.85 for the actual measurement with two duplicates).

$$c\text{-}RUP_1 = \frac{(40 \times 1/77.7) + (55 \times 1/38.85)}{(1/77.7 + 1/38.85)}$$
$$= 50$$

2. Calculating a Corrected dRUP for the Standard Blood Meal.

Again, a weighted average of the prior and the measurement is calculated with respective weights based on the reciprocal of their variances.

$$c\text{-}dRUP_1 = \frac{(70 \times 1/331.7) + (80 \times 1/165.85)}{(1/331.7 + 1/165.85)}$$
$$= 76.7$$

3. Calculating a Corrected dRUP for the Standard Casein.

This is also a weighed mean of prior and actual measurement.

$$c\text{-}dRUP_2 = \frac{(98 \times 1/38.2) + (100 \times 1/19.1)}{(1/38.2 + 1/19.1)}$$
$$= 99.3$$

4. Calculating the Corrected RUP for Sample A.

$$cRUP_A = \frac{cRUP_1}{RUP_1} \times RUP_A$$

$$cRUP_A = \frac{50}{55} \times 85 = 77.3\%$$

5. Calculating the Regression to Correct d-RUP of Sample A.

5.1 Let $X = \begin{bmatrix} 1 & dRUP_1 \\ 1 & dRUP_2 \end{bmatrix} = \begin{bmatrix} 180 \\ 1100 \end{bmatrix}$ 5.2 $Y = \begin{bmatrix} c\text{-}dRUP_1 \\ c\text{-}dRUP_2 \end{bmatrix} = \begin{bmatrix} 76.7 \\ 99.3 \end{bmatrix}$ 5.3 Then $\begin{bmatrix} B_0 \\ B_1 \end{bmatrix} = [X^1 X]^{-1} X^1 Y = \begin{bmatrix} -13.7 \\ 1.13 \end{bmatrix}$ where $X^1$ is the transpose matrix of X and $[\ ]^{-1}$ is the matrix inverse of $[\ ]$.

5.4 Calculating c-dRUP$_A$:

$$c - dRUP_A = B_0 + (B_1 * dRUP_A)$$
$$= -13.7 + (1.13 * 90)$$
$$= 88.0\%$$

6. Results

The estimated protein undegradability of sample A=cRUP$_A$=77.3%.

The estimated protein digestibility of sample A=c-dRUP$_A$=88.0%.

Efficiency of the Correction Method in Reducing Inter-Assay Variation.

To determine the standard error of a corrected digestibility measurement, the corrected RUP digestibility was measured on 11 samples of blood meal, 3 samples of hydrolyzed feather meal, and 2 samples of poultry meal. Analyses were done in duplicates one month apart. Results are reported in Table 2 for the 16 samples, and for the two replicates. The variance due to inter-assay (across duplications) was estimated using a one-way analysis of variance with sample ID as the main factor. The mean square error is an unbiased estimate of the variance due to batches (replicates). Based on these results, this variance equals 14.86 when measurements are corrected using the two standards. Thus, the variance of the corrected measurement is only 4.5% of the variance of the uncorrected measurement (14.86/331.24), demonstrating the efficiency of the method in reducing errors and improving precision of measurements.

TABLE 2

Estimated c-dRUP on two replicates for 11 samples of blood meal, 3 samples of hydrolyzed feather meal, and 2 samples of poultry meal.

| Sample ID | Month 1 | Month 2 |
| --- | --- | --- |
| BM22 | 64.78 | 67.93 |
| BM23 | 31.09 | 27.39 |
| BM24 | 36.41 | 38.23 |
| BM25 | 68.09 | 66.71 |
| BM26 | 71.61 | 69.34 |
| BM30 | 80.21 | 83.04 |
| BM32 | 75.29 | 83.98 |
| BM33 | 66.01 | 67.11 |
| BM35 | 71.50 | 69.06 |
| BM36 | 75.71 | 67.88 |
| BM38 | 80.83 | 71.37 |
| FM45 | 65.52 | 61.50 |
| FM56 | 82.77 | 73.61 |
| FM58 | 74.42 | 67.87 |
| PM66 | 59.28 | 57.02 |
| PM76 | 64.69 | 71.93 |

TABLE 2-continued

Estimated c-dRUP on two replicates for 11 samples of blood meal, 3 samples of hydrolyzed feather meal, and 2 samples of poultry meal.

| Sample ID | Month 1 | Month 2 |
| --- | --- | --- |
| Variance of replicate within sample ID: | 14.86 | |
| Standard error of replicate within sample ID: | 3.85% | |

Implementations of Computer Program Product and Computer System

The present invention or any part(s) or function(s) thereof may be implemented using hardware, software or a combination thereof and may be implemented in one or more computer systems or other processing systems. However, the manipulations performed by the present imnvention were often referred to in terms, such as adding or comparing, which are commonly associated with mental operations performed by a human operator. No such capability of a human operator is necessary, or desirable in most cases, in any of the operations described herein which form part of the present invention. Rather, the operations are machine operations. Useful machines for performing the operation of the present invention include general purpose digital computers or similar devices.

Figure 5:
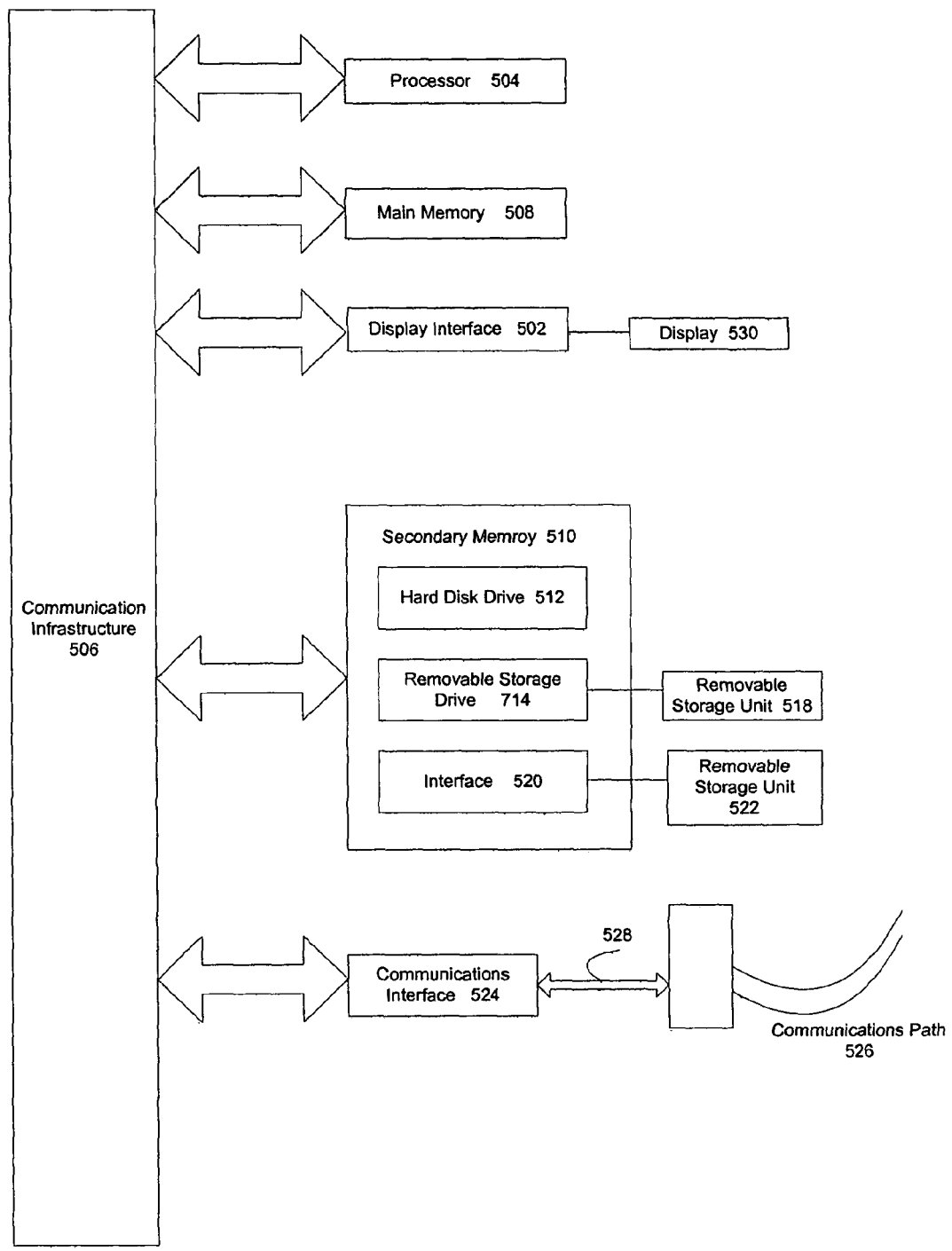
FIG. 5 is a schematic of Computer System according to the invention.

In fact, in one embodiment, the invention is directed toward one or more computer systems capable of carrying out the functionality described herein. An example of a computer system 500 is shown in FIG. 5.

The computer system 500 includes one or more processors, such as processor 504. The processor 504 is connected to a communication infrastructure 506 (e.g., a communications bus, cross-over bar, or network). Various software embodiments are described in terms of this exemplary computer system. After reading this description, it will become apparent to a person skilled in the relevant art(s) how to implement the invention using other computer systems and/or architectures.

Computer system 500 can include a display interface 502 that forwards graphics, text, and other data from the communication infrastructure 506 (or from a frame buffer not shown) for display on the display unit 530.

Computer system 500 also includes a main memory 508, preferably random access memory (RAM), and may also include a secondary memory 510. The secondary memory 510 may include, for example, a hard disk drive 512 and/or a removable storage drive 514, representing a floppy disk drive, a magnetic tape drive, an optical disk drive, etc. The removable storage drive 514 reads from and/or writes to a removable storage unit 518 in a well known manner. Removable storage unit 518 represents a floppy disk, magnetic tape, optical disk, etc. which is read by and written to by removable storage drive 514. As will be appreciated, the removable storage unit 518 includes a computer usable storage medium having stored therein computer software and/or data.

In alternative embodiments, secondary memory 510 may include other similar devices for allowing computer programs or other instructions to be loaded into computer system 500. Such devices may include, for example, a removable storage unit 522 and an interface 520. Examples of such may include a program cartridge and cartridge interface (such as that found in video game devices), a removable memory chip (such as an erasable programmable read only memory (EPROM), or programmable read only memory (PROM)) and associated socket, and other removable storage units 522 and interfaces 520, which allow software and data to be transferred from the removable storage unit 522 to computer system 500.

Computer system 500 may also include a communications interface 524. Communications interface 524 allows software and data to be transferred between computer system 500 and external devices. Examples of communications interface 524 may include a modem, a network interface (such as an Ethernet card), a communications port, a Personal Computer Memory Card International Association (PCMCIA) slot and card, etc. Software and data transferred via communications interface 524 are in the form of signals 528 which may be electronic, electromagnetic, optical or other signals capable of being received by communications interface 524. These signals 528 are provided to communications interface 524 via a communications path (e.g., channel) 526. This channel 526 carries signals 528 and may be implemented using wire or cable, fiber optics, a telephone line, a cellular link, an radio frequency (RF) link and other communications channels.

In this document, the terms "computer program medium" and "computer usable medium" are used to generally refer to media such as removable storage drive 514, a hard disk installed in hard disk drive 512, and signals 528. These computer program products provide software to computer system 500. The invention is directed to such computer program products.

Computer programs (also referred to as computer control logic) are stored in main memory 508 and/or secondary memory 510. Computer programs may also be received via communications interface 524. Such computer programs, when executed, enable the computer system 500 to perform the features of the present invention, as discussed herein. In particular, the computer programs, when executed, enable the processor 504 to perform the features of the present invention. Accordingly, such computer programs represent controllers of the computer system 500.

In an embodiment where the invention is implemented using software, the software may be stored in a computer program product and loaded into computer system 500 using removable storage drive 514, hard drive 512 or communications interface 524. The control logic (software), when executed by the processor 504, causes the processor 504 to perform the functions of the invention as described herein.

In another embodiment, the invention is implemented primarily in hardware using, for example, hardware components such as application specific integrated circuits (ASICs). Implementation of the hardware state machine so as to perform the functions described herein will be apparent to persons skilled in the relevant art(s). In yet another embodiment, the invention is implemented using a combination of both hardware and software.

From the foregoing description, it can be seen that the present invention comprises a new and unique methods and computer products for improving the determination of the undegraded percentage of an ingestable substance within a sample at an actual or simulated point along a digestive process in an organism or ruminant. It will be recognized by those skilled in the art that changes could be made to the above-described embodiments of the invention without departing from the broad inventive concepts thereof. It is understood, therefore, that this invention is not limited to the particular embodiments disclosed, but is intended to cover all modifications which are within the spirit and scope of the invention and that this invention is not limited to the particular embodiments disclosed, but it is intended to cover any modifications which are within the spirit and scope of the present invention as defined by the appended claims.

What is claimed is:

1. A process for correcting a directly measured (DM) undegraded percentage (U %) value of an ingestable substance (IS) within a feedstuff at an actual or simulated point along a digestive process in an organism, said process comprising the steps of:
    i) obtaining a DM U % value of the IS in a sample specimen of the feedstuff;
    ii) obtaining a DM U % value of the IS in a standard specimen of the feedstuff;
    iii) looking up at least one stored prior U % value of the IS in respective prior standard specimens of the feedstuff;
    iv) calculating a correction factor using Bayesian statistical analysis applied to the DM U % value of the IS in the standard specimen and the at least one stored prior U % value of the IS in the respective prior standard specimens;
    v) multiplying the DM U % value of the IS in the sample specimen of the feedstuff by the correction factor to obtain a corrected DM U % value of the IS in the sample specimen of the feedstuff; and
    vi) displaying the corrected DM U % value of the IS in the sample specimen of the feedstuff, wherein the steps are performed using a computer.

2. The process according to claim 1, wherein at least one value originates from the data of an in-vivo assay.

3. The process according to claim 1, wherein at least one value originates from the data of an in-vitro assay.

4. The process according to claim 1, wherein at least one value originates from the data of a single-step in-vitro assay.

5. The process according to claim 1, wherein at least one value originates from the data of a multi-step in-vitro assay.

6. The process according to claim 1, wherein at least one value originates from the data of an in-vitro assay modeling a normal digestive process.

7. The process according to claim 1, wherein at least one value originates from the data of an in-vitro assay modeling a digestive process associated with an extra-normal health condition.

8. A process according to claim 1, wherein at least one measurement is entered into a computer system.

9. A process according to claim 1, wherein at least one value is processed by a computer system.

10. A process according to claim 1, wherein the standard specimen comprises a substance that is less degradable when digestibility is compared with the sample specimen.

11. A process according to claim 1, wherein the standard specimen comprises blood meal and the substance is protein.

12. A process according to claim 1, wherein the standard specimen comprises a substance that is more degradable when digestibility is compared with the sample specimen.

13. A process according to claim 1, wherein the standard specimen comprises casein and the substance is protein.

14. A process according to claim 1, wherein said process further comprises modulating the protein content in the milk of a ruminant by feeding the ruminant a food mixture comprising a component that is the same as the sample.

15. A process according to claim 1, wherein said process further comprises modulating the protein production of a ruminant by feeding the ruminant a food mixture comprising a component that is the same as the sample.

16. A process according to claim 1, wherein said process further comprises modulating the body condition of a ruminant by feeding the ruminant a food mixture comprising a component that is the same as the sample specimen of the feedstuff.

17. A process according to claim 1, wherein said process further comprises modulating the overall feed intake or pasture usage by a ruminant by feeding the ruminant a food mixture comprising a component that is the same as the sample.

18. A process according to claim 1, wherein said process further comprises modulating the waste production by a ruminant by feeding the ruminant a food mixture comprising a component that is the same as the sample.

19. A process according to claim 1, wherein said process further comprises:
   taking a measure of the U % of the IS in the sample specimen of the feedstuff.

20. The process of claim 1, wherein the correcting step comprises the steps of:
   (ivA) correcting the DM U % value of the IS in the standard substance specimen using Bayesian statistical analysis applied to the DM U % value of the IS in the standard substance specimen and the at least one prior U % value of the IS in the respective prior standard substance specimens; and
   (ivB) proportionally modifying the DM U % value of the sample specimen by the same proportion applied in correcting the DM U % value of the IS in the standard substance specimen.

21. The process of claim 1 further comprises the steps of:
   ii) obtaining a DM U % value of the IS in a standard specimen of at least one other feedstuff; and
   iii) looking up at least one stored prior U % value of the IS in respective prior standard specimens of the at least one other feedstuff;
   wherein the correcting step corrects the DM U % value of the IS in the sample specimen using Bayesian statistical analysis applied to the DM U % value of the IS in the standard specimen, the at least one stored prior U % value of the IS in the respective prior standard specimens, the DM U % value of the IS in the at least one other standard specimen and the at least one stored prior U % value of the IS in respective at least one other prior standard specimen.

22. The process of claim 21, wherein the correcting step comprises the steps of:
   (ivA) determining a correction factor using Bayesian statistical analysis applied to the DM U % value of the IS in the standard specimen, the at least one stored prior U % value of the IS in the respective prior standard specimens, the DM U % value of the IS in the at least one other standard specimen and the at least one stored prior U % value of the IS in respective at least one other prior standard specimen;
   (ivB) multiplying the DM U % value of the IS in the sample specimen by the correction factor.

* * * * *